(12) United States Patent
Adang et al.

(10) Patent No.: US 6,218,365 B1
(45) Date of Patent: Apr. 17, 2001

(54) SERINE PROTEASE INHIBITORS

(75) Inventors: Anton Egbert Peter Adang, Eindhoven; Jacobus Albertus Maria Peters, Oss, both of (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/142,068

(22) PCT Filed: Feb. 26, 1997

(86) PCT No.: PCT/EP97/00939

§ 371 Date: Aug. 31, 1998

§ 102(e) Date: Aug. 31, 1998

(87) PCT Pub. No.: WO97/31939

PCT Pub. Date: Sep. 4, 1997

(30) Foreign Application Priority Data

Mar. 1, 1996 (EP) .................................................. 96200545

(51) Int. Cl.$^7$ .............................. A61K 38/00; C07K 5/00; C07K 7/00
(52) U.S. Cl. ............................. 514/16; 514/17; 514/18; 514/20; 530/330; 530/331; 530/300; 530/328; 530/329
(58) Field of Search .................................. 514/16, 17, 18, 514/20, 212, 269, 315, 349, 424, 563, 601, 604, 605, 619, 626; 530/330, 331, 328, 329; 546/242, 297; 548/543, 550

(56) References Cited

U.S. PATENT DOCUMENTS 6,034,067 * 3/2000 Grootenhuis et al. .................. 514/18

FOREIGN PATENT DOCUMENTS

| 0672658 | * | 9/1995 | (EP) . |
| 9425051 | * | 11/1994 | (WO) . |
| 9429336 | * | 12/1994 | (WO) . |
| 9535311 | * | 12/1995 | (WO) . |
| 9619483 | * | 6/1996 | (WO) . |

OTHER PUBLICATIONS

Jones et al., *Letters in Peptide Science*, vol. 2, pp 147–154, 1995.*

Costanzo et al., *J. Med. Chem.*, vol. 39, No. 16, 1996, pp 3039–3043.*

* cited by examiner

*Primary Examiner*—Avis M. Davenport
(74) *Attorney, Agent, or Firm*—Mary E. Gormley

(57) ABSTRACT

The invention relates to a cornound having formula (I), wherein A, B, X, Y and r are as defined in the description, or a prodrug thereof or a pharnnaceutically acceptable salt thereof. The compounds of the invention have anticoagulant activity and can be used in treating or preventing thrombin-related diseases.

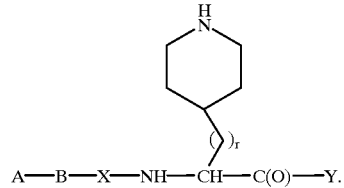

(I)

A—B—X—NH—CH—C(O)—Y.

15 Claims, No Drawings

SERINE PROTEASE INHIBITORS

FIELD OF THE INVENTION

The invention relates to a serine protease inhibitor having a piperidine side chain, a pharmaceutical composition containing the same, as well as the use of said inhibitor for the manufacture of a medicament for treating and preventing thrombin-related diseases.

BACKGROUND OF THE INVENTION

Serine proteases are enzymes which, amongst other things, play an important role in the blood coagulation cascade. Members of this group of proteases are for example thrombin, trypsin, factors VIIa, IXa, Xa, XIaa, XIIa, and protein C.

Thrombin is the serine protease which regulates the last step in the coagulation cascade. The prime finction of thrombin is the cleavage of fibrinogen to generate fibrin monomers, which form an insoluble gel by cross-linking. In addition, thrombin regulates its own production by activating factors V and VIII earlier in the cascade. It also has important actions at cellular level, where it acts on specific receptors to cause platelet aggregation, endothelial cell activation and fibroblast proliferation. Thus thrombin has a central regulatory role in haemostasis and thrombus formation Since inhibitors of thrombin may have a wide range of therapeutical applications, extensive research has been performed in this are& In the development of synthetic inhibitors of serine proteases, and more specifically of thrombin, the interest in small synthetic peptides that are recognized by proteolytic enzymes in a manner similar to that of natural substrates, has increased. As a result, new peptide-like inhibitors have been prepared, such as the transition state inhibitors of thrombin. The search for more effective and more selective thrombin inhibitors continues unabated in order to obtain thrombin inhibitors which can be administered in lower dosages and which have fewer and less severe side effects. Furthermore, special attention is paid to oral bioavailabilirty. Potent intravenous thrombin inhibitors are clinically effective in acute care settings requiring the treatment of thrombin-related diseases. However, particularly the prevention of thrombin-related diseases such as myocardial infarct, thrombosis and stroke require long-term therapy, preferably by orally dosing an anticoagulant.

Most of the peptide-like thrombin inhibitors disclosed in prior publications contain side chains of arginine. A problem of the those arginine containing thrombin inhibitors is that they have low oral bioavailabldity. A number of thrombin inhibitors contain lysine side chains instead of arginine have been reported in literature. The lower basicity of lysine, relative to argiine, was expected to result in increased oral bioavailability. Examples of lysine containing thrombin inhibitors are the inhibitor N—Me—D—Cha—Pro—Lys—COOH and derivatives thereof, disclosed by Jones et al., J. Enzyme Inhibition, 9 (1995), 43–60, and the inhibitors N—Me—D—Phe—Pro—Lys—X, X being a carboxamide or carboxylic acid, disclosed by Lewis et al., Thrombosis and Haemostasis, 74(4) (1995), 1107–12. However, the expected improvement was not observed, the oral bioavailabilities of several lysyl thrombin inhibitors being similar to that reported for inhibitors having an arginine side-chain (Lewis et al., Thrombosis and Haemostasis, 74(4) (1995), 1107–12). Other thrombin inhibitors are disclosed in WO 94/25051 wherein the lysine or arginine side chain is replaced by aminocyclohexyl moieties which may be regarded as lysine isosters.

SUMMARY OF THE INVENTION

It has now been found that serine protease inhibitors, and in particular thrombin, Xa and Vila inhibitors, having a piperidine side chain, according to the fornmla I

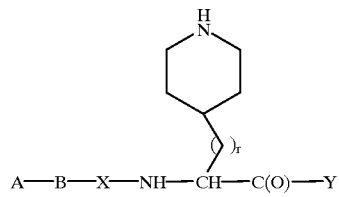

A—B—X—NH—CH—C(O)—Y wherein

A is H, optionally substituted D,L α-hydroxyacetyl, $R^1$, $R^1$—O—C(O)—, $R^1$—C(O)—, $R^1$—$SO_2$—, $R^2OOC$—$(CHR^2)_m$—$SO_2$—, $R^2OOC$—$(CHR^2)_m$—, $H_2NCO$—$(CHR^2)_m$—, or an N-protecting group, wherein $R^1$ is selected from (1–12C)alkyl, (2–12C)alkenyl, (2–12C)alkynyl and (3–8-C)cycloalkyl, which groups may optionally be substituted with (3–8C)cycloalkyl, (1–6C)alkoxy, oxo, OH, COOH, $CF_3$ or halogen, and from (6–14C)aryl, (7–15C)aralkyl and (8–16)aralkenyl, the aryl groups of which may optionally be substituted with (1–6C)alkyl, (3–8C)cycloalkyl, (1–6C)alkoxy, OH, COOH, $CF_3$ or halogen; each group $R^2$ is independently H or has the same meaning as $R^1$; m is 1, 2 or 3;

B is a bond, an amino-acid of the formula —NH—CH[$(CH_2)_pC(O)OH$]C(O)— or an ester derivative thereof with p being 0, 1, 2 or 3, —N((1–12C)alkyl)—$CH_2CO$—, —N((2–12C)alkenyl)—$CH_2$—CO—, —N((2–12C)alkynyl)—$CH_2$—CO—, —N(benzyl)—$CH_2CO$—, D—1-Tiq, D-3-Tiq, D—Atc, Aic, D-1-Piq, D-3-Piq or a L- or D-amino acid having a hydrophobic, basic or neutral side chain, which amino acid may optionally be N-(1–6C)alkyl substituted;

or A and B together are the residue $R^3R^4N$—$CHR^5$—C(O)—, wherein $R^3$ and $R^4$ independently are $R^1$, $R^1$—O—C(O)—, $R^1$—C(O)—, $R^1$—$SO_2$—, $R^2OOC$—$(CHR^2)_m$—$SO_2$—, $R^2OOC$—$(CHR^2)_m$—, $H_2NCO$—$(CHR^2)_m$—, or an N-protecting group, or one of $R^3$ and $R^4$ is connected with $R^5$ to form a 5- or 6membered ring together with "N—C" to which they are bound, which ring may be fused with an aliphatic or aromatic 6membered ring; and $R^5$ is a hydrophobic, basic or neutral side chain;

X is an L-amino acid with a hydrophobic side chain, serine, threonine, a cyclic amino acid optionally containing an additional heteroatom selected from N, 0 or S, and optionally substituted with (1–6C)alkyl, (1–6C)alkoxy, benzyoxy or oxo, or X is —$NR^2$—$CH_2$—C(O)— or the fragment

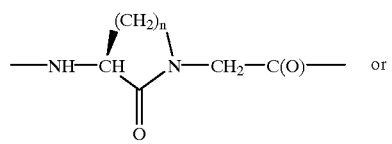

or

-continued

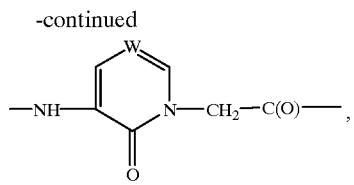

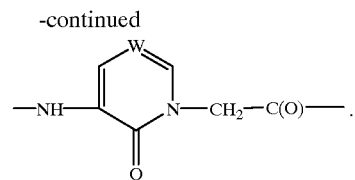

wherein n is 2, 3, or 4, and W is CH or N;

Y is H, —CHF$_2$, —CF$_3$, —CO—NH—(1–6C)alkyleneC$_6$H$_5$, —COOR$^6$ with R$^6$ being H or (1–6C)alkyl, —CONR$^7$R$^8$ and R$^7$ and R$^8$ being independently H or (1–6C)alkyl or R$^7$ and R$^8$ together being (3–6C)alkylene, or Y is a heterocycle selected from 2-thiazole, 2-thiazoline, 2-benzothiazole, 2-oxazole, 2-oxazoline and 2-benzoxazole, which heterocycles may optionally be substituted with (1–6C)alkyl, phenyl, (1–6C)alkoxy, benzyloxy or oxo; and r is 0, 1, 2 or 3;

or a prodrug thereof or a pharmaceutically acceptable salt thereof are potent and selective inhibitors. In addition, some of the compounds of the invention show good bioavailability after oral administration.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in wiro anticoagulants.

DETAIL DESCRIPTION OF THE INVENTION

Preferred compounds according to the invention have the formula I, wherein X is an L-amino acid with a hydrophobic side chain, serine, threonine or —NR$^2$—CH$_2$—C(O)—.

Other preferred compounds of formula I are those wherein A is as previously defined; B is a bond, an amino acid of the formula —NH—CH[(CH$_2$)$_p$C(O)OH]—C(O)— or an ester derivative thereof and p being 0, 1, 2 or 3, —N((1–6C,alkyl)—CH$_2$—CO—, —N((2–6C)alkenyl)—CH$_2$CO—, —N(benzyl)—CH$_2$—CO—, D-1-Tiq, D-3-Tiq, D—Atc, Aic, D-1-Piq, D-3-Piq or a D-anino acid having a hydrophobic side chain, which amino acid may optionally be N—(1–6C)alkyl substituted; or A and B together are the residue R$^3$R$^4$N—CHR$^5$—C(O)—; and X is a cyclic amino acid optionally containing an additional heteroatom selected from N, O or S, and optionally substituted with (1–6C)alkyl, (1–6C)alkoxy, benzyloxy or oxo, or X is —NR$^2$CH$_2$—C(O)— or the fragment

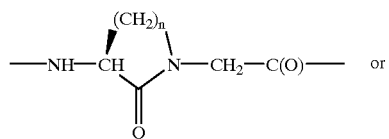

More preferred are compounds of formula I wherein A is H, 2-hydroxy-3-cyclohexyl-propionyl-, 9-hydroxy-fluorene-9-carboxyl, R$^1$, R$^1$-SO$_2$—, R$^2$OOC—(CHR$^2$)$_m$—SO$_2$—, R$^2$OOC—(CHR$^2$)$_m$—, H$_2$NCO—(CHR$^2$)$_m$—, or an N-protecting group, wherein R$^1$ is selected from (1–12C) alkyl, (2–12C)alkenyl, (6–14C)aryl, (7–15C)aralkyl and (8–16)aralkenyl; each group R$^2$ is independently H or has the same meaning as R$^1$; B is a bond, D-1-Tiq, D-3-Tiq, D—Atc, Aic, D-1-Piq, D-3-Piq or a D-amino acid having a hydrophobic side chain, which amino acid may optionally be N-(1–6C)alkyl substituted; or A and B together are the residue R$^3$R$^4$N—CHR$^5$-C(O)—; Y is —CO—NH—(1–6C)alkylene-C$_6$H$_5$, —COOR$^6$, —CONR$^7$R$^8$, or Y is a heterocycle selected from 2-thiazole, 2-thiazoline, 2-benzothiazole, 2-oxazole, 2-oxazoline and 2-benzoxazole. In particular preferred are those compounds, wherein A is H, R$^1$—SO$_2$— or R$^2$OOC—(CHR$^2$)$_m$—; B is a bond, D-1-Tiq, D-3-Tiq, D—Atc, Aic, D-1-Piq, D-3-Piq or a D-amino acid having a hydrophobic side chain; or A and B together are the residue R$^3$R$^4$N-CHR$^5$—C(O)—, wherein at least one of R$^3$ and R$^4$ is R$^2$OOC—(CH$^2$)$_m$— or R$^1$—SO$_2$— and the other independently is (1–12C)alkyl, (2–12C)alkenyl, (2–12C)alkynyl, (3–8C)cycloalkyl, (7–15C)arallyl, R$^1$—SO$_2$— or R$^2$OOC—(CHR$^2$)$_m$—, and R$^5$ is a hydrophobic side chain; Y is —CO—NH—(1–6C)alkylene-C$_6$H$_5$, —COOR$^6$ and R$^6$ being H or (1–3C)alkyl, —CONR$^7$R$^8$, with R$^7$ and R$^8$ being independently H or (1–3C)alkyl or R$^7$ and R$^8$ together being (3–5C)alkylene, or Y is a heterocycle selected from 2-thiazole, 2-benzothiazole, 2-oxazoe or 2benzoxazole.

When A is R$^2$OOC—(CHR$^2$)$_m$—, preferably B is a D-amino acid having a hydrophobic side chain; or A and B together are the residue R$^3$R$^4$N—CHR$^5$—C(O)—, wherein at least one of R$^3$ and R$^4$ is R$^2$OOC—(CHR$^2$)$_m$— and the other independently is (1–12C)alkyl, (2–6C)alkenyl, (3–8C) cycloalkyl, benzyl, R$^1$—SO$_2$— or R$^2$OOC—(CHR$^2$)$_m$—; and X is 2-azetidine carboxyic acid, proline, pipecolic acid, 4-thiazolidine carboxylic acid, 3,4-dehydro-proline, 2 octsydroindole carboxylic acid or —[N(3–8C)cycloalkyl]-CH$_2$—C(O)—. More preferred are compounds wherein A is HOOC—CH$_2$—; B is D—Phe, D—Cha, D—Coa, D—Dpa, p—Cl—D—Phe, p—OMethyl—D—Phe, p—OEthyl—D—Phe, D—Nle, m—Cl—D—Phe, 3,4-di—OMe—D—Phe, or D—Chg; or A and B together are the residue R$^3$R$^4$N—CHR$^5$—C(O)—, wherrin at least one of R$^3$ and R$^4$ is HOOC—CH$_2$— and the other independently is (1–4C) alkyl, (1–4C)alkyl—SO$_2$— or HOOC—CH$_2$— and R$^5$ is (3–8C)cycloalkyl, (3–8C)cycloalkyl(1–4C)alkyl, phenyl, benzyl, optionally substituted with chlorine or (1–4C) alkoxy. Most preferred are those compounds wherein A is HOOC—CH$_2$—; B is D—Cha; X is proline or —[N (cyclopentyl)]—CH$_2$—C(O)—.

When A is R$^1$—SO$_2$—, preferably B is a bond, D-1-Tiq, D3-Tiq, D—Atc, Aic, D-1-Piq, D-3-Piq or a D-amino acid having a hydrophobic side chain; or A and B together are the residue R$^3$R$^4$N—CHR$^5$—C(O)—, wherein at least one of R$^3$ and R$^4$ is R$^1$—SO$_2$— and the other independently is (1–12C)alkyl or R$^1$—SO$_2$—; X is 2-azetidine carboxylic acid, proline, pipecolic acid, 4-thiazolidine carboxylic acid, 3,4-dehydroproline, 2-octahydroindole carboxylic acid, —[N(3–8C)cycloalkyl]—CH₂—C(O)—, or the fragment

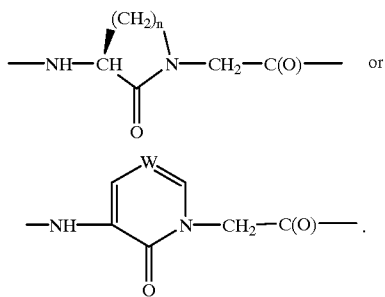

More preferred are compounds wherein A is Ethyl—SO₂— or Beenzyl-SO₂—; B is a bond, D—Phe, D—Cha, D—Coa, D—Dpa, p—Cl—D—Phe, p—OMethyl—D—Phe, p—OEthyl—D—Phe, D—Nle, m—Cl—D—Phe, 3,4di—OMe—D—Phe, or D—Chg; or A and B together are the residue R³R⁴N—CHR⁵—C(O)—, wherein at least one of R³ and R⁴ is Ethyl—SO₂— or Benzyl—SO₂— and the other independently is (1–12C)alkyl or R¹—SO₂— and R⁵ is (3–8C)cycloalkyl, (3–8C)cycloalkyl(1–4C)alkyl, phenyl, benzyl, diphenylmethinyl, which groups are optionally substituted wath chlorine or (1–4C)alkoxy. Most preferred are those compounds wherein A is Ethyl—SO₂—, B is D—Cha; X is proline or —[N(cyclopentyl)]—CH₂—C(O)—.

Most preferably r is 1 in the compounds of formula I.

The N-protecting group as defined in the definition of moiety A is any N-protecting group as used in peptides. Suitable N-protecting groups can be found in T. W. Green and P. G. M. Wuts: Protective Groups in Organic Synthesis, Second Edition (Wiley, N.Y., 1991) and in The Peptides, Analysis, Synthesis, Biology, Vol. 3 E. Gross and J. Meienhofer, Eds., (Academic Press, New York, 1981).

The term optionally substituted D,L α-hydroxyac means a group of the formula HO—CRᵃRᵇ—C(O)—, wherein Rᵃ and Rᵇ independently are H, a hydrophobic side chain, or Rᵃ and Rᵇ together form a 5- or 6-membered ring, which is optionally fused with one or two aliphatic or aromatic 6-membered rings, and which 5- or 6-membered ring consists of carbon atoms and optionally one heteroatom selected from N, O and S. Preferred D,L α-hydroxyacetyl groups are 2-hydroxy-3-cyclohexyl-propionyl- and 9-hydroxy-fluorene-9carboxyl.

The term (1–12C)alkyl means a branched or unbranched alkyl group having 1 to 12 carbon atoms, such as methyl, ethyl, t-butyl, isopentyl, heptyl, dodecyl, and the like Preferred alkyl groups are (1–6C)alkyl groups, having 1–6 carbon atoms. Most preferred in the definition of R⁶, R⁷ and R⁸ are (1–3C)alkyl groups, having 1–3 carbon atoms, such as methyl, ethyl, isopropyl. A (2–12C)alkenyl group is a branched or unbranched unsaturated hydrocarbon group having 2 to 12 carbon atoms. Preferred are (2–6C)alkenyl groups. Examples are ethenyl, propenyl, allyl, and the like.

The term (1–6C)alkylene means a branched or unbranched alkylene group having 1 to 6 carbon atoms, such as —(CH₂)ₘ— and m is 1 to 6, —CH(CH₃)—, —CH(CH₃)—(CH₂)—, etc. Preferred alkylene groups in the definition of Y are ethylene and methylene.

A (2–12C)alkyryl group is a branched or unbranched hydrocarbon group containing a triple bond and having 2 to 12 carbon atoms. Preferred are (2–6C)alkynyl groups, such as ethynyl and propynyl.

A (6–14C)aryl group is an aromatic moiety of 6 to 14 carbon atoms. The aryl group may fiilther contain one or more hetero atoms, such as N, S, or O. Examples of alyl groups are phenyl, naphthyl, (iso)quinolyi, indanyl, and the like. Most preferred is the phenyl group.

(7–15C)AralWyl and (8–16C)aralkenyl groups are alkyl and alkenyl groups restively, substituted by one or more aryl groups, the total number of carbon atoms being 7 to 15 and 8 to 16, respectively.

The term (1–6C)alkoxy means an alkoxy group having 1–6 carbon atoms, the alkl moiety of which having the meaning as previously defined.

The term (3–8Cdycloalkyl means a cycloalkyl group having 3–8 carbon atoms, being cydopropyl, cyclobutyl, cyclopentyl, cyclohexyl, cydoheptyl or cyclo-octyl. Cyclopentyl and cyclohexyl are preferred cycloalkyl groups.

The term halogen means fluorine, chlorine, bromine or iodine.

The term ester derivative means any appropriate ester derivative, preferably (1–4C)alkyl-esters, such as methyl-, ethyl- or t-butyl-esters.

The terms 1- and 3-Tiq mean 1,2,3,4tetrahydroisoquinoline-1- or -3-carboxylic acid, respectively; 1- and 3-Piq are 1- and 3-carboxyperhydroisoquinoline, respectively; Atc is 2-aminotetralin-2-carboxylic acid; Aic is amino indane carboxylic acid; Phe is phenylalanine; Cha is cyclohexylalanine; Dpa is diphenylalanine; Coa is cyclooctylalanine; Chg is cyclohexylglycine; Nle is norleucine; Asp is aspartic acid.

The term hydrophobic side chain means a (1–12C)alkyl, optionally substituted with one or more (3–8C)cycloalkyl groups or (6–14C)aryl groups (which may contain a heteroatom, e.g. nitrogen) such as cyclohexyl, cyclo-octyl, phenyl, pyridinyl, naphthyl, tetrahydronaphthyl, and the like, which hydrophobic side chain may optionally be substituted with substituents such as halogen, trifluoromethyl, lower alkyl (for instance methyl or ethyl), lower alkoxy (for instance methoxy), phenyloxy, benzyloxy, and the like.

In the definitions, the term substituted means: substituted by one or more substituent. Amino acids having a basic side chain are for example, but not limited to, arginine and lysine, preferably arginine. The term amino acids having a neutral side chain refers to amino acids such as methionine sulphon and the like.

Cyclic amino acids are for example 2-azetidine carboxylic acid, proline, pipecolic acid, 1-amino-1-carboxy-(3–8C)cycloalkane (preferably 4C, 5C or 6C), 4-piperidine carboxylic acid, 4thiazolidine carboxylic acid, 3,4dehydro-proline, azaproline, 2-octahydroindole carboxylic acid, and the like. Preferred are 2-azetidine carboxylic acid, proline, pipecolic acid, 4-thiazolidine carboxylic acid, 3,4-dehydro-proline and 2-octahydroindole carboxylic acid. The term prodrug means a compound in which the nitrogen atom of the piperidine group of the compound of formula I is protected, e.g. by a hydroxy, (1–6C)alkoxy or (1–6C)alkoxycarbonyl group.

The invention fuirther includes a process for preparing a compound of formula I, including coupling of suitably protected amino acids or amino acid analogs, followed by removing the protective groups.

The compounds according to formula I may be prepared in a manner conventional for such compounds. The modified amino acid having the piperidine side chain is introduced in a way similar to methods known for other amino acids.

To that end, suitably Nα protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tert-butyloxycarbonyl group (Boc), benzyloxycarbonyl (Z) group and substituted analogs or the base-labile 9-fluorenyl-methyloxycarbonyl (Fmoc) group. The Z group can also be removed by catalytic hydrogenation. Other suitable amino protective groups include Nps, Bmv, Bpoc, Msc, etc. A good overview of amino protective groups is given is given in The Peptides, Analysis, Synthesis, Biology, Vol. 3 E. Gross and J. Meienhofer, Eds., (Academic Press, New York, 1981). Protection of carboxyl groups can take place by ester fonnation e.g. base-labile esters like methyl- or ethylesters, acid labile esters like tert-butylesters, or hydrogenolytically-abile esters like benzylesters. Protection of the piperidine side chain may be accomplished by using the aforementioned groups. Activation of the carboxyl group of the suitably protected amino acids or peptides can take place by the azide, mixed anhydride, active ester, or carbodimide method, especially with the addition of catalytic and racemization-suppressing compounds like 1-hydroxybenzotriazole, N-hydroxysuccinimide, 3-hydroxy4-oxo-3,4-dihydro-1,2,3-benzo-triazine, N-hydroxy-5-norbornene-2,3-dicarboximide. See, e.g. The Peptides, Analysis, Synthesis, Biology (see above) and Pure and Applied Chem. 59(3), 331–344 (1987).

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess one or more chiral carbon atoms, and may therefore be obtained as a pure enantiomer, or as a mixture of enantiomers, or as a mixture containing diastereomers. Methods for obtaining the pure enantiomers are well known in the art, e.g crystallization of salts which are obtained from optically active acids and the racemic mixture, or chromatography using chiral columns. For diastereomers straight phase or reversed phase columns may be used.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, eg. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof used in suitable amounts.

The invention is further illustrated by the following examples.

EXAMPLES

The terms —PpaΨ[COCO]—OH, —Ppa—OMe and —Ppa—(2-thiazolyl) mean

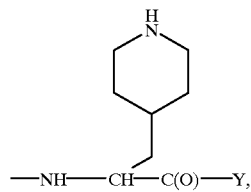

wherein Y is COOH, OCH$_3$ and 2-thiazolyl, respectively.

Azt=2-azetidine carboxylic acid; Boc=tert-butyloxycarbonyl; Cbz=benzyloxycarbonyl; TsOH=p-toluenesulphonic acid

EXAMPLE 1

HOOC—CH$_2$—D—Cha—Pro—PpaΨ[COCO]—OH (a) H—D—Cha—OMe.HCl

To cold (−20° C.) and dry methanol (195 ml) was added dropwise thionylchloride (28 ml). H—D—Cha—OH.HCl (40 g) was added and the reaction mixture was heated under reflux for 5 hours The mixture was concentrated in vacuo and coevaporated with methanol (3 times). The residue was crystallized from methanol/diethyl ether yielding H—D—Cha—OMe.HCl as a white crystalline powder (40.9 g). TLC: Rf=0.66, silica gel, n-butanol/acetic acid/water 10/1/3 v/v/v.

(b) N—(t-Butyloxycarbonylmethyl)—D—Cha—OMe t-Butyl-bromoacetate (36 g) was added to a stiffed solution H—D—Cha—Me.HCl (40.9 g) in 400 ml of acetonitrile. The pH of the mixture was adjusted to 8.5 with N,N-diisopropylethylamine. The mixture was stirred for 16 hours at room temperature and evaporated in vacuo. The residue was dissolved in dichloromethane and the solution was washed with water, dried on sodium sulphate and evaporated in vacuo. Chromatography over silica gel eluting with heptanelethyl acetate 9/1 v/v gave 64 g of N—(t-butyloxycarbonylmethyl) D—Cha—OMe.

TLC: Rf=0.25, silica gel, ethyl acetate/heptane 1/1 v/v.

(c) N—Ct-Butyloxvcarbonylmethyl)—N—Boc—D—Cha—OMe

The pH of a solution of N—(t-butyloxycarbonylmethyl) D—Cha—OMe (64 g) and di—t-butyl dicarbonate (40.3 g) was adjusted to 8.5 with N,N-disopropylethylamine. The mixture was stirred for 16 hours at room tempeature. The solvent was removed in vacuo. Dichloromethaane and water were added to the residue. The organic layer was separated, washed with cold 1N hydrochloric acid, water, 5% sodium hydrogencarbonate and water, dried on sodium sulphate and the filtrate was evaporated to an amorphous solid of N—(t-butyloxycarbonylmethyl)—N—Boc—D—Cha—OMe with a yield of 59.6 g.

TLC: Rf=0.50, silica gel, ethyl acetate/heptane 1/1 v/v.

(d) N—(t-Butyloxcarbonylmethyl)—N—Boc—D—Cha—OH

A solution of N—(t-butyloxycarbonylmethyl)—N—Boc—D—Cha—OMe (59.6 g) in 900 ml of dioxane/water 9/1 v/v was treated with sufficient 6 N sodium hydroxide to keep the pH at 12 for 6 hours at room temperature. After acidification, the mixture was poured into water and was extracted with dichloromethane. The organic layer was washed with water and was dried on sodium sulphate. The filtrate was evaporated and yielded 54 g of N—(t-butyloxycarbonyl-methyl)—N—Boc—D—Cha—OH.

TLC: Rf=0.60, silica gel, dichloromethane/methanol 9/1 v/v.

(e) N—(t-Butyloxycarbonylmethyl)—N—Boc—D—Cha—Pro—OBzl

To a cold (0° C.) solution of N—(t-butyloxycarbonylmethyl)—N—Boc—D—Cha—OH (13.5 g) in N,N-dimethylformamide (150 ml) were successively added 1-hydroxy benzotriazole (HOBT) (7.09 g), dicyclohexyl carbodiimide (DCCI) (7.61 g), H—Pro—OBzl.HCl (9.31 g) and triethylamine (6 ml). The mixture was stirred at 0° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 5% sodium hydrogencarbonate, water, 3% citric acid and brine, dried over sodium sulphate and concentrated in vacuo. The residue was chromatographed on silica gel eluting with heptane/ethyl acetate 3/1 v/v as eluent. The fractions containing N—(t-butyloxycarbonylmethyl)—N—Boc—D—Cha—Pro—OBzl were pooled and evaporated. Yield: 15 g.

TLC: Rf=0.70, silica gel, heptane/ethyl acetate 1/1 v/v.

(f) N—(t-Butyloxyocarbonylmethyl)—N—Boc—D—Cha—Pro—OH

10% palladium on charcoal (750 mg) was added to a solution of N—(t-Butyloxycarbonylmethyl)—N—Boc—D—Cha—Pro—OBzl (15 g) in methanol (150 ml). The mixture was hydrogenated at atmospheric pressure at room temperature for 1 hour. The palladium catalyst was removed by filtration and the solvent was removed by evaporation at reduced pressure yielding 11.2 g N—(t-butyloxycarbonylmethyl)—N—Boc—D—Cha—Pro—OH.

TLC: Rf=0.65, silica gel, ethyl acetate/pyridine/acetic acid/water 213/20/6/11 v/v/v/v.

(g) Diethyl 2-acetamido-2-[(pyridin4-yl)methyl]-malonate

A 46 8 portion of sodium metal was added to 3.5 l of ethanol and heated. Diethyl acetamido malonate (217 g) and 4-picolyl chloride hydrochloride (164 g) were added to the resultant solution of sodium ethoxide. The reaction mixture was heated to 100° C. for 4 hours, cooled, filtered and concentrated in vacuo. The residue was dissolved in dichloromethane filtered over diacel and silica gel and concentrated in vacuo. The residue was treated with 1 l of diethyl ether, filtered and washed with diethyl ether. Yield 142 g.

TLC: Rf=0.5 in ethyl acetate:pyridine:acetic acid:water 63/5/1.5/2.75 v/v/v/v on silica gel.

(h) Ethyl 2acetamido-2-[(pyridin4-yl)methyl]-malonate

A solution of 142 g of diethyl 2-acetamido-2-[(pyridin4-yl)methyl]-malonate, 46 g of potassium hydroxide in 2 l of ethanol and 800 ml of water was stirred for 16 hours. The mixture was acidified and concentrated in vacuo. Coevaporation with methanol and toluene gave 187 g of ethyl 2-acetamido-2-[(pyridin4-yl)methyl]-malonate (contains potassium chloride).

TLC: Rf=0.95 in ethyl acetate:pyridine:acetic acid 63/5/1.5/2.75 v/v/v/v on silica gel.

(i) Ethyl 2-N-acetylamino-3-(pyridin-4yl)-propanoate

A solution of 394 g of ethyl 2-acetamido-2-[(pyridin-4-yl)methyl]-malonate in 1.5 l of N,N-dizmeylfonmamide was refluxed for 1½ hour and concentrated in vacuo. The residue was dissolved in water and the pH adjusted to 11.5. The mixture was extracted with ethyl acetate, dried on sodium sulphate and concentrated in vacuo. Yield: 158.8 g.

TLC: Rf=0.35 in ethyl acetate:pyridine:acetic acid:water 63/5/1.5/2.75 v/v/v/v on silica gel.

(j) Ac—Ppa—OEt

A solution of 39,5 g of ethyl 2-N-acetylamino-3-(pyridin4-yl)propanoate in 1 l ethanol was reduced under an hydrogen atmosphere using 4 g of palladium on activated carbon 10% as a catalyst. After 18 hours, the catalyst was removed by filtration and the filtrate was concentrated to dryness to yield 40 g of the desired compound.

(k) H—Ppa—OH

A solution of 81.5 g of Ac—Ppa—OEt in 6 N hydrochloric acid was refluxed for 4 hours The reaction mixture was concentrated in vacuo and yielded 90 g of H—Ppa—OH.HCl.

TLC: Rf=0,97 in 1-butanol:pyridine:acetic acid:water 8/3/1/4 v/v/viv on silica gel.

(l) Cbz—Ppa(Boc)—OH

The pH of a solution of 90 g of H—Ppa—OH, 51.23 g of copper (II) sulphate pentahydrate and 166 g of di—t-butyl dicarbonate in water (1730 ml) and dioxane (1250 ml) was adjusted to 9 with 2N sodium hydroxide. The mixture was stirred for 16 hours at room temperature. The precipitate was collected and washed well with water. The filtercake was dissolved in dioxane and the pH adjusted to 12.5 with 4N sodium hydroxide and 200 g of benzyloxycarbonyloxysuccinimide was added. The mixture was stirred for 16 hours. The precipitate was collected and washed with dioxane. The filtrate was concentrated to a small volume and the pH was adjusted to 2.5. The residue was diluted with ethyl acetate. The organic layer was washed with water dried on sodium sulphate and evaporated to dryness and gave 160 g of the tide compound.

TLC: Rf=0.77 in ethyl acetate:pyrdine:acetic acid:water 63/20/6/11 v/v/vlv on silica gel.

(m) Cbz—Ppa(Boc)—OMe

To a solution of 160 g of Cbz—Ppa(Boc)—OH in dichloromethane/methanol 9/1 v/v (3 l) was added 120 g of 2-(1H-benzotriazol-1-yl)1,1,3,3-tetramethyl uronium tetrafluoroborate (TBTU), whereafter the pH was adjusted to 8.5 with triethylamine. The mixture was stirred for 1 hour at room temperature. The organic layer was washed with 2N hydrochloric acid, water, 5% sodium hydrogencarbonate solution and water, dried on sodium sulphate and concentrated in vacuo. The residue was chromatographed on silica gel eluting with dichloromethane/ethyl acetate 9/1 v/v. The fractions containing the methyl ester were pooled and the solvent removed in vacuo. The residue was crystallized from diisopropyl ether/diethyl ether and gave a first crop of 75 g of the desired product. The mother liquor was chromatographed in toluene/ethyl acetate 812 v/v and gave 34 g of Cbz—Ppa(Boc)—OMe.

TLC: Rf=0.77 in dichloro methane:methanol 95/5 v/v on silica gel.

(n) 2-Acetoxy-3-(benzyloxycarbonylamino)4-(1-t-butyloxycarbonyl(piperidin-4-yl)-butanitrile At −78° C., 908 ml of precooled diisobutylaluminum hydride (1.0 M solution in hexane) was added to a stirred solution of 109 g of Cbz—Ppa(Boc)—OMe in dichloromethane (3 l) at such a rate that the temperature was kept below −70° C. The solution was stirred for 1 hour at −70° C. and 1 l of a saturated solution of citric acid was added. The mixture was poured into 2 l of a citric acid solution and extracted with dichloromethane. The combined extracts were washed with water, 5% sodium hydrogencarbonate solution and water, dried on sodium sulphate and filtered. The filtrate was cooled to 0° C., and subsequently 15 g of benzyltriethyl ammonium chloride, 58 ml of acetic anhydride and a solution of 118 g of sodium cyanide in water (1.5 l) were added. The mixture was vigorously stirred for 30 min. The organic layer was separated, washed twice with water, dried on sodium sulphate and concentrated in vacuo. The residue was chromatographed on silica gel eluting with hexane/ethyl acetate 6/4 v/v, to give the title compound as a solid: 98 g.

TLC: Rf=0.65 in dichloro methane/methanol 95/5 v/v on silica get.

(o) Cbz—PpaΨ[CHOHCO]—OMe

A stirred suspension of 98 g of 2-acetoxy-3 (benzyloxycarbonylamino)4-(1-t-butyloxy-carbonyl (piperidin4-yl)-butanitrile in 3 L of a mixture of diethyl ether/methanol 9/1 v/v was treated with gaseous hydrogen chloride (260 g) at −20° C. The mixture was stirred at 0–5° C. for 24 hours Then the mixture was cooled to −20° C. and 408 ml of water was added. The reaction mixture was stirred for 4 hours at 20° C. and the organic layer was separated. The pH of the aqueous layer was adjusted to 8 with 25% ammonia, followed by extraction of this layer with 1-butanol. The combined extracts were washed with brine, dried on sodium sulphate and evaporated to dryness and gave 57 g of Cbz—PpaΨ[CHOHCO]—OMe.

TLC: Rf=0.5 in ethyl acetate/pyridine/acetic acid/water 63/20/6/11 v/vtv/v on silica.

(p) Cbz—Ppa(Boc)Ψ[CHOHCO]—OMe

The pH of a solution of Cbz—PpaΨ[CHOHCO]—OMe (57.9 g) and 40 g of di—t-butyl dicarbonate in 500 ml of N,N-dimethylformamide was adjusted to 8.5 with triethylamine. The mixture was stirred for 45 min at room temperature. The solvent was removed in vacuo. The residue was dissolved in ethyl acetate washed with 0.1 N hydrochloric acid, water, 5% sodium hydrogencarbonate and water. The organic layer was dried on sodium sulphate and evaporated to dryness. The residue was chromatographed on silica gel eluting with heptane/ethyl acetate 614 v/v and gave 31 g of an oil.

(q) N—(t-Butyloxycarbonylmethyl)—N—Boc—D—Cha—Pro—Ppa(Boc)Ψ[CHOHCO]—OMe

A solution of 120 mg of Cbz—Ppa(Boc)Ψ[CHOHCO]—OMe, 0.27 ml 1 N hydrochloric acid and 12 mg of palladium on activated carbon 10% as catalyst in N,N-dimethylformnamide (4 ml) was hydrogenated under atmospheric pressure. When the reaction was completed, the catalyst was removed and the pH of the solution was adjusted to 8.5 with triethylamine. The solution was added to a stirred solution of 137 mg of N—(t-butyloxycarbonylmethyl)—N—Boc—D—Cha—Pro—OH, 40 mg 1-hydroxy-benzotriazole and 61 mg of 1.3-dicyclohexylcarbodiimide in 10 ml of N,N-dimethylformamide. The reaction mixture was stirred for 16 hours at room temperature. The solvent was removed in vacuo and dichloromethane was added to the residue. The precipitate was filtered and the filtrate washed with 1 N hydrochloric acid, water, 5% sodium hydrogencarbonate solution and water. The organic layer was dried on sodium sulphate and evaporated in vacuo and gave 220 mg of the desired compound.

TLC: Rf=0.6 in ethyl acetate//pyridinetacetic acid/water 63/5/1.5/2.75 v/v/v/v on silica gel.

(r) N—(t-Butyloxycarbonylmethyl)—N—Boc—D—Cha—Pro—Pap(Boc)Ψ[CHOHCO]—OH

The pH of a solution of 220 mg of N—(t-butyloxycabonylmethyl)—N—Boc—D—Cha—Pro—Ppa (Boc)Ψ[CHOHCO]—OMe in 15 ml of dioxane/water 9/1 v/v was adjusted to 12 with 1 N sodium hydroxide. The reaction mixture was stirred for 1.5 hours The pH was adjusted to 2.5 with 1 N hydrochloric acid and the mixture was poured into water and extracted with ethyl acetate. The organic layer was washed with water, dried on sodium sulphate and evaporated to dryness. Yield 210 mg of the title compound TLC: RF=0.21 in ethyl acetatelpyridine/acetic acid/water 63/5/1.5/2.75 v/v/v/v on silica gel.

(s) N—(t-Butyloxycarbonylmethyl)—N—Boc—D—Cha—Pro—Ppa(Boc)Ψ[COCO]—OH

To a solution of 210 mg of N—(t-butyloxycarbonylmethyl)—N—Boc—D—Cha—Pro—Ppa (Boc)Ψ[CHOHCO]—OH in 20 ml of dichloromethane was added 177 mg of 1,1,1-triacetoxy-1,1-dihydro-1,2-benziodoxol-3 (1H)-one (Dess-Martin reagent). The mixture was stirred for 4 hours at room temperature, poured into a solution of sodium thiosulphate (5% in water) and extracted with dichloromethane. The organic layer was washed with water, dried on sodium sulphate and concentrated in vacuo. Yield 340 mg.

TLC: Rf=0.4 in ethyl acetatelpyridine/acetic acid/water 63/20/6/11 vlvlv/v on silica gel.

(t) HOOC—CH$_2$—D—Cha—Pro—PpaΨ[COCO]—OH

A solution of 340 mg of N—(t-butyloxycarbonylmethyl)—N—Boc—D—Cha—Pro—Ppa (Boc)Ψ[COCO]—OH in 20 ml of 90% tiifluoroacetic acid was stirred for 4 hours at room temperature. The solvent was removed in vacuo and the residue was purified on preparative HPLC supelcosil LC-18-BD column using a gradient elution system of A: 20%; B: 80%; C: 0% to A: 20%; B: 55%; C: 25% over 45mnin at a flowrate of 20 ml/min. (A: 0.5 M phosphate buffer pH=2.1; B: water; C: acetonitrile-:water 3:2 v/v), yielding a mixture of diastereomers 53.7 mg.

Rt (LC): 22.65 min; A: 20%; B: 80%; C: 0% to A: 20%; B: 20%; C: 60% in 40 min.

EXAMPLE 2

HOOC—CH$_2$—D—Cha—N-cyclopentyl—Gly—PpaΨ[COCO]—OH (a) N-cyclopentyl—Gly—OMe.HCl

H—Gly—OMe.HCl (46.4 g) was dissolved in 400 ml methanol, cyclopentanone (34 g) and sodium cyanoborohydride (14 g) were added and the reaction was allowed to proceed for 16 h at room temperature. The reaction mixture was quenched with 6 M hydrochloric acid until pH 2 and stirred for 30 min at room temperature. The solvent was removed by evaporation under reduced pressure, the residue was dissolved in water and washed with diethyl ether. The pH was adjusted to pH>10 by addition of 6 M sodium hydroxide solution, the product wvas exracted with dichworomethane, washed with brine, dried over sodium sulphate, filtered and concentrated under reduced pressure. The compound was crystallized from ethyl acetate as the HCl-salt. Yield: 43.5 g.

TLC: Rf=0.71, silica gel, ethyl acetatelpyridine/acetic acid/water 88/31/18/7 v/v/v/v.

(b) N—(t-Butyloxycarbonylmethyl)—N—Boc—D—Cha—N-cyclopentyl—Gly—OH

N—(t-Butyloxycarbonylmethyl)N—Boc—D—Cha—N-cyclopentyl—Gly—OH was prepared according to the procedure described in example 1 for the dipeptide moiety, using TBTU as activator.

(c) HOOC—CH$_2$—D—Cha—N-cyclopentyl—Gly—PpaΨ[COCO]—OH

The DCCI/HOBt-coupling between N—(t-butyloxycarbonylmethyl)—N—Boc—D—Cha—N- cyclopentyl—Gly—OH and H—Ppa(Boc)Ψ[CHOHCO]—OMe.HCl, saponification, Dess-Martin oxidation, deprotection and purification were done according to the procedures described in example 1 to give the title compound as a diastereomeric mixture.

$R_t$ (LC): 29.72 min. 20% A/80% B to 20% A/20% B/60% C in 40 min.

EXAMPLE 3
HOOC—CH$_2$—D—Phe—Pro—PpaΨ[COCO]—OH

N—(t-Butyloxycarbonylmethyl)—N—Boc—D—Phe—Pro—OH was prepared as desaibed in example 1 starting from H—D—Phe—OH.HCl.

The DCCI/HOBt-coupling between N—(t-butyloxycarbonylmethyl)—N—Boc—D—Phe—Pro—OH and H—Ppa(Boc)Ψ[CHOHCO]—OMe.HCl, saponification, Dess-Martin oxidation, deprotection and purification were done according to the procedures described in example 1. The title compound was obtained as a diastereomeric mixture.

$R_t$ (LC): 17.77 and 18.19 min. 20% A 80% B to 20% A/20% B 60% C in 40 min.

EXAMPLE 4
HOOC—CH$_2$—m—Cl—D,L—Phe—Pro—PpaΨ[COCO]—OH

H—m—Cl—D,L—Phe—OH.HCl was prepared according a similar procedure as described in example 53 starting from 3-chlorobenzylbromide. Next, the filly protected tripeptide was assembled according to the same procedures as described in example 1. The title compound was obtained as a diastereomeric mixture.

$R_t$ (LC): 22.24/23.07 min. 20% A/80% B to 20% A 120% B/60% C in 40 min.

EXAMPLE 5
HOOC—CH$_2$—p—Cl—D—Phe—Pro—PpaΨ[COCO]—OH (a) N—(t-Butyloxycarbonylmethyl)—N—Boc—p—Cl—D—Phe—OH According to analogous procedures as described in example 1, H—p—Cl—D—Phe—OH. HCl (10 g) was converted into N—(t-butyloxycarbonylmethyl)—N—Boc—p—Cl—D—Phe—OH. Yield: 16.7 g.

TLC: Rf=0.27, silica gel, ethyl acetate/methanol 9/1 v/v.
(b) N—(t-Butyloxycarbonylmethyl)—N—Boc—p—Cl—D—Phe—OSu (Su=succinimide) A solution of N—(t-butyloxycarbonylmethyl)—N—Boc—p—Cl—D—Phe—OH (14.67 g) in 250 ml acetonitrile was treated with N-hydroxysucciniride (4.11 g) and 1-(3-dimethylaminopropyl)-3-ethylcarbodiimide hydrochloride (6.86 g) overnight at room temperature. The reaction mnixture was evaporated to dryness and the residue was dissolved in ethyl acetate. The organic phase was washed with water, dried over sodium sulphate and concentrated to afford 19.11 g active ester, which was directly used in the next step
(c) N—(t-Butyloxycarbonalmethyl)—N—Boc—p—Cl—D—Phe—Pro—OH H—ProOH.HCl (10.79 g) was dissolved in 100 ml of N,N-dimethylformamide and 100 ml of water. The pH of the reaction mixture was adjusted to 8 with a 1N sodium hydroxide solution, whereafter N4-butyloxycarbonylmethyl)N—Boc—p—Cl—D—Phe—OSu (19.11 g), dissolved in 120 ml of N,N-dimethylformamide, was added dropwise. The reaction was stirred overnight at Eroom temperature at pH 8. The reaction mixture was cooled and adjusted to pH 2 with 1 N hydrochloric amid. The aqueous layer was extracted with dichloromethane. The organic phase was washed with water, dried over sodium sulphate and evaporated in vacuo. Silmgel purification, using a gradient ethyl acetate/methanol 9/1 to 1/1 v/v, afforded 7.04 g of the desired dipeptide TLC: Rf=0.24, silica gel, ethyl acetate/methanol 8/2 v/v.
(d) HOOC—CH$_2$—p—Cl—D—Phe—Pro—PpaΨ[COCO]—OH The DCCI/HOBt-coupling between N—(t-butyloxycarbonylmethyl)—N—Boc—p—Cl—D—Phe—N-cyclopentyl—Gly—OH and H—Ppa(Boc)Ψ[CHOHCO]—OMe.HCl, saponification, Dess-Martin oxidation, deprotection and purification were done according to the procedures described in example 1. The title compound was obtained as a diastereomeric mixture.

$R_t$ (LC): 23.67 min.20% A/80% B to20% A/20% B/60% C in40 min.

EXAMPLE 6
HOOC—CH$_2$—D—p—MeO—Phe—Pro—PpaΨ[COCO]—OH

The tripeptide was prepared similar to the route followed for example 1 starting from H—p—MeO—D—Phe—OH to yield the title compound as a diastereomeric mixture.

$R_t$ (LC): 19.18 min.20% A/80% B to20% A/20% B/60% C in40 min.

EXAMPLE 7
HOOC—CH$_2$—D,L—Coa—Pro—PpaΨ[COCO]—OH
(a) Cyclo-octylmethyl bromide Cyclo-octylmethanol (8.16 g) was dissolved in 47% HBr-solution (70 ml) and refluxed for 1 hour at 130° C. The reaction mixture was poured onto ice water (500 ml) and saturated sodium hydrogencarbonate solution (500 ml) was added. The aqueous solution was extracted with dichloromethane. The combined organic phases were washed with water, brine and dried over sodium sulphate, filtered and concentrated in vacuo. The residue was chromatographed on silica gel eluting with toluene as eluent. The fractions containing cyclo-octyimethyl bromide were pooled and evaporated. Yield: 9.85 g.

TLC: Rf:=0.95 , silica gel, toluene
(b) (R,S)-Ethyl-2-acetylamino-2-cyano-3-cylooctyl-propionate Potassium t-butylate (6.85 g) and ethyl acetamidocyanoacetate (8.1 g) were dissolved in dimethylsulfoxide (100 ml) at room temperature. Cyclooctylmethyl bromide was dissolved in dimethylsulfoxide (25 ml) and added dropwise to the reaction mixture. The mixture was stirred at room temperature for 44 hours. After pouring onto 500 ml water the precipitate was filtered and dried to yield (R,S)-Ethyl-2-acetylamino-2-cyano-3-cyclooctylpropionate (2.95 g)

TLC: Rf=0.50, silica gel, heptane/ethyi acetate 3/7 v/v.
(c) H—D,L—Coa—OH.HCl (R,S)-Ethyl-2-acetylamino-2cyano-3-cyclooctylpropionate (2.95 g) was suspended in 100 ml of 20% hydrochloric acid and refluxed for 22 hours. The reaction mixture was cooled to 5° C. and the precipitate formed was filtered, washed with diethyl ether and dried. Yield: 2.69 g of H—D,L—Coa—OH.HCl.

TLC: Rf=0.27, silica gel, ethyl acetate/pyridine/acetic acid/water 63/20/6/11 v/v/v/v.

In a similar manner as described in example 1 HOOC—CH$_2$—D,L—Coa—Pro—PpaΨ[COCO]—OH was prepared. The title compound was obtained as a diastereomeric mixture.

$R_t$ (LC): 15.19 min; 20% A/60% B/20% C to20% A/80% C in 30 min.

R$_t$ (LC): 25.71 min; 20% A/80% B to 20% A/20% B/60% C in 40 min.

EXAMPLE 8

The tripeptide was prepared similar to the route followed for example 1 starting from H—D—Nle—OH to yield the title compound as a diastereomeric mixture.

R$_t$ (LC): 19.50 and 20.24 min; 20% A/80% B to 20% A/50% B/30% C in 40 min.

EXAMPLE 9

HOOC—CH$_2$—D—Dpa—Pro—PpaΨ[COCO]—OH

The tripeptide was prepared similar to the route followed for example 1 starting from H—D—Dpa—OH to give the title compound as a diastereomeric mixture.

R$_t$ (LC): 29.18 min; 20% A/80% B to 20% A/20% B/60% C in 40 min.

EXAMPLE 10

D—Hpl—Pro—Ppa—(2-thiazolyl)
(Hpl=2-hydroxy-3-phenyl lactic acid)
(a) THP—D—Hpl—Pro—OH The synthesis of THP—D—Hpl—Pro—OH starting with H—D—Cha—OH is described in example 20.
(b) D—Hpl—Pro—Ppa—(2-thiazoly)

Coupling of THP—D—Hpl—Pro—OH with H—Ppa (Cbz)-(2-thiazolyl).TFA, followed by deprotection and purification, according to the methods as described in example 45, yielded D—Hpl—Pro—Ppa—(2-thiazolyl) as a mixture of diastereomers.

R$_t$ (LC): 23.42 and 24.36 min, 20% A, 60% B and 20% C to 100% C in 40 min.

EXAMPLE 11

HOOC—CH$_2$—p—Me—D—Phe—Pro—PpaΨ[COCO]—OH (a) Fmoc—p—Me—D—Phe—OMe

Fmoc—p—Me—D—Phe—OH (5 g) was dissolved in dichloromethane/methanol 9/1 v/v (50 ml). 2-(1H-benzotriazol-1-yl 1,1,3,3-tetramethyluronium tetrafluoroborate (4.4 g) was added and the solution adjusted to pH 8 by addition of triethylamine. The reaction mixture was stirred for 16 hours at room temperature. The mixture was washed successively with cold 1N hydrochloric acid solution, water, 5% sodium hydrogencarbonate, and water and dried over sodium sulphate. The filtrate was evaporated yielding 5.6 g of Fmoc—p—Me—D—Phe—OMe as an oil.

TLC: Rf=0.55, silica gel, ethyl acetatetheptane 6/4 v/v.
(b) H—p—Me—D—Phe—OMe

Fmoc—p—Me—D—Phe—OMe (5.6 g) was dissolved in 35 ml of N,N-dimethylformamide/piperidine 4/1 and stirred for 30 min at room temperature. The mixture was evaporated and the residue was taken up in ethyl acetate and washed with 0.1 M hydrochloric acid The pH of the combined waterlayers was adjusted to pH 9 by addition of 1 M sodium hydroxide solution.

After extraction with dichloromethane, the resulting oil was chromatographed on silica gel eluting with ethyl acetate/methanol 95/5 v/v. The fractions containing H—p—Me—D—Phe—OMe were pooled and evaporated. Yield : 2.33 g.

TLC: Rf=0.10, silica gel, heptane/ethyl acetate 3/2 v/v.

Next, the fully protected tripeptide was assembled according to the same procedures as described in example 1. The title compound was isolated as a diastereomeric mixture.

R$_t$ (LC): 22.55 min; 20% A/80% B to 20% A/20% B/60% C in 40 min.

EXAMPLE 12

BenzylSO$_2$norLeu(cyclo)—Gly—S—PpaΨ[COCO]—OH norLeu(cyclo)-Gly means a structural fragment of the formula

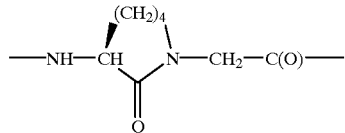

(a) 3-(piperidin4-yl)-propanoic acid

A mixture of 12.5 g of 3-(4-pyridyl)acrylic acid and 1.25 g of Pd/C 10% as a catalyst in 1 l of ethanol and 83 ml of 1 N hydrochloric acid was shaken in a hydrogen atmosphere for 64 hours. The catalyst was removed by filtration and the filtrate was evaporated to dryness yielding 13 g of the desired compound.

TLC: Rf=0.7, silica gel, butanol/pyridine/acetic acid/water 4/1/1/2 v/v/v.
(b) 3-[1-(t-Butyloxycarbonyl)piperidin4-yl]propanoic acid A suspension of 3-(piperidin4-yl)propanoic acid in 500 ml of N,N-dimethylformamide was treated with 30.9 g of di t-butyl dicarbonate. The pH of the reaction was adjusted at pH 8.5 using triethylamine and stirred for 4 hours at room temperature. The mixture was poured in 65 ml of a cooled 2 N sodium hydroxide solution and washed with ethyl acetate. The aqueous phase was acidified with 2 N hydrochloric acid pH 2 and extracted with ethyl acetate. The combined organic layers were washed with brine, dried on sodium sulphate and evaporated in vacuo to yield 37 g of the desired compound.

TLC: Rf=0.7, dichloromethanetmethanol 9/1 v/v on silica gel
(c) (4S)-3-[3-[1-(t-Butyloxycarbonyl)pipeidin-4-yl]-1-oxo-propyl]-4-(phenylmethyl)-2-oxazolidinone The conversion of 27 g of 3-[-1-(t-butyloxycarbonyl)piperidin4-yl]propanoic acid in 325 ml of dry tetrahydrofuran was accomplished by treatment with 13.7 ml of pivaloyl chloride and 15.6 ml of triethylamine at −72° C. The mixture was stirred for 1 hour at 0° C. To a solution of 18.5 g of S-4-benzyl-2-oxazolidinone in 325 ml of dry tetrahydrofuran was added dropwise at −72° C. under nitrogen atmosphere 75 ml of a 1.4 M solution of n-BuLi in hexane. The mixture was stirred for 20 min. at −70° C. The suspension of the above prepared mixed anhydride was added and the reaction mixture was stirred for 20 min. at −70° C. The reaction was quenched by pouring into water and extraction with ether. The combined organic layers were washed with cold 1 N hydrochloric acid, water, 5% sodium hydrogencarbonate solution and water. The solution was dried on sodium sulphate and evaporated in vacuo to yield 47.5 g as an oil. Flashchromatography on silica gel eluting with heptanelethyl acetate 1/1 v/v yielded 28.2 g of the title compound.

TLC: Rf=0.7 in heptane/ethyl acetate 1/1 v/v on silica.
(d) (3(2S),4S)-3-[2-Azido-3[1-(t-butyoxycarbonyl) pipeindin4-yl]-1-oxo-propyl]-4-(phenylmethyl)-2-oxazolidinone To 110 ml of dry tetrahydrofuran stirred at −78° C. under nitrogen atmosphere was added 136 ml of potassium hexamethyidisilazide 0.5 M in toluene. To the resulting solution was added via cannula a precooled solution −78° C. of 25 g of (4S)-3-[3-[1-(t-butyloxyearbonyl)piperidin4-yl]-1-oxo-propyl]-4-(phenylmethyl)-2-oxazolidinone in 350 ml of dry tetrahydrofuran and the stirring was continued for 30 min at −75° C. under nitrogen atmosphere. To the above solution of the potassiumenolate stirred at −75° C. was added a solution of 24 g of trisylazide (litt. JCS Perkin Trans (1991), 1629) in 215 ml of dry tetrahydroftiran. After 5 min. the reaction was quenched with 17 ml of acetic acid. The mixture was stirred for 20 min at −75° C. and 16 hours at room temperature.

Flashchromatography on silica gel eluting with heptane/ethyl acetate 7/3 v/v and treatment with heptane gave 19 g of the title compound as a solid.

TLC: Rf=0.6 in dichloromethanelethyl acetate 9/1 v/v on silica (e) (2S)-2-Azido3-[(1-t-butyloxycarbonyl)piperidin-4-yl]-propanoic acid To a solution of 19 g of (3(2S),4S)-3-[2-azido-3-[1-(t-butyloxycarbonyl)piperidin-4-yl]-1-oxo-propyl]-4-(phenylmethyl)-2-oxazolidinone in 600 ml of tetrahydrofuran, 18 ml of hydrogenperoxide 30% and 170 ml of water was added 3.7 g of solid lithium hydroxide at 0° C. under nitrogen atmosphere. The mixture was stirred for 30 min at 0° C. under nitrogen atmosphere. A solution of 25.3 g of sodium sulphite in 133 ml of water and 530 ml of a 5% sodium hydrogencarbonate solution were added. The temperature was raised to room temperature and the stirring was continued for 30 min. The solvent was removed in vacuo and the residue was dissolved in water and washed with ethyl acetate. The aqueous phase was acidified with 6 N hydrochloric acid to pH 2 and extracted with ethyl acetate. The extracts were washed with brine, dried on sodium sulphate and evaporated in vacuo. Ciystallization of the residue from ether/heptane gave 11.9 g of a crystalline solid.

TLC: Rf=0.8 in dichloromethanelmethanol 95/5 v/v on silica.

(f) (2S )-N-Methyl-N-methox-2-azido-3-[1-(t-butyloxycarbonyl)peridin-4-yl]-propanamide To a solution of 5.7 g of (2S)-2-azido-3-[(1-(t-butyloxycarbonyl)piperidin-4-yl]-propanoic acid in 150 ml of dichloromethane was added 2.1 g of N,O-dimethylhydroxylamiine.HCl and 6.4 g of TBTU. The pH was adjusted at pH=8.5 with triethylamine. The mixture was stirred for 30 min at room temperature, then washed with 1 N hydrochloric acid, water, 5% sodium hydrogencarbonate and water. The organic layer was dried on sodium sulphate, filtered and evaporated in vacuo to yield 7.4 g of the title compound as an oil.

TLC: Rf=0.6 in dichloromethane/methanol 95/5 v/v on silica.

(g) Methyl (2S)-2-azido-3-[(1-(t-butyloxycarbonyl)piperidin-4-yl]-propanoic acid The pH of a mixture of (2S)-2-azido-3-[(1-(t-butyloxycarbonyl)piperidin-4-yl]-propanoic acid (example 12e) and 6.94 g of TBTU in 100 ml of dichloromethane/methanol 9/1 v/v was adjusted at pH 8.5 with triethylamine. The mixture was stirred for 30 min at room temperature, then washed with 1 N hydrochloric acid, water, 5% sodium hydrogencarbonate solution and water. The organic layer was dried on sodium sulphate filtered, evaporated in vacuo and gave 7.4 g of the title compound as an oil.

TLC: Rf=0.85 in dichloromethane/methanol 95/5 vlv on silica (h) H—S—Ppa(Boc)—OMe A solution of methyl (2S)-2-Azido-3-[(1-(t-butyloxycarbonyl)piperidin-4-yl]-propanoic acid (7.4 g), 0.5 g of Pd/C (10%), and 21.9 ml of 1N hydrochloric acid in tetrahydrofuran (300 ml) was hydrogenated at atmospheric pressure. The catalyst was filtered off and the solvent removed in vacuo to yield after ether treatment 6.8 g of a ctistalline solid TLC: Rf=0.85 in ethyl acetate/pyridine/acetic acid/water 252/20/6/11 vlv/v/v.

(i) Cbz—S—Ppa(Boc)—OMe

The pH of a solution of 6.5 g of H—S—Ppa(Boc)—OMe and 5.6 g of bennyloxycarbonyloxy-succinimide in 70 ml of N,N-dimethylformamide was adjusted at pH 8.5 with triethylamine. The mixture was stirred for 6 hours at room temperature, poured into water and extracted with ethyl acetate. The combined organic layers were washed with 1 N hydrochloric acid, water, 5% sodium hydrogencarbonate and water, dried on sodium sulphate and evaporated in vacuo to yield 7.9 g of the title compound as an oil.

TLC: Rf=0.85 in heptane/ethyl acetate 1/1 v/v on silica (j) Cbz—S—Ppa(Boc)—H

To a solution of 7.5 g of Cbz—S—Ppa—(Boc)—OMe in 225 ml of dry dichloromethane at −75° C. under nitrogen atmosphere was added dropwise 68.1 ml of a 1 M solution of diisobutylaluminumhydride in hexane keeping the temperature below −70° C. The rnixtre was stirred for 1 hour at −75° C. under nitrogen atmosphere. The mixture was poured out in a citric acid solution and extracted with ethyl acetate. The combined extracts were washed with water, 5% sodium hydrogen carbonate solution and water and concentrated in vacuo to yield 7.5 g of the title compound.

TLC: Rf=0.45 in dichloromethanelmethanol 95/5 v/v on silica (k) (3S)-2-Aceto-3-(benyoxycarbonylamino)-4-[1-t-butyloxycarbonyl(piperidin-4-yl)]-butanitrile Cbz—S—Ppa(Boc)—H (7.5 g) (example 12(j)) was converted to (3S)-2-Acetoxy-3 (benzyloxycarbonylamino)-4-[1-t-butyloxycarbonyl(piperidin-4-yl)]-butanitrile according to a procedure similar to the one described in example 1(n).

TLC: Rf=0.75 in dichloromethane/methanol 95/5 v/v on silica (l) Cbz—S—Ppa(Boc)Ψ[CHOHCO]—OMe (3S)-2-Acetoxy-3(benzloxycarbonylamino)-4-[1-t-butyloxycarbonyl(piperidin-4-yl)]-butanitrile was converted to the title compound according to the procedure described in example 1(o).

TLC: Rf=0.5 in dichloromethanctmethanol 95/5 v/v on silica.

(m) H—S—Ppa(Boc)Ψ[CHOHCO]—OMe.HCl

H—S—Ppa(Boc)Ψ[CHOHCO]—OMe.HCl was prepared according to the hydrogenation procedure described in example 1(q).

(n) N—Boc—L—α-Amino—ε-caprolactam

To a stirred solution of L—α-Amino-ε-caprolactam (10 g) in dioxanelwater (2/1 v/v) (30 nm) was added 1 N sodium hydroxide solution (7.8 ml) followed by di—t-butyl dicarbonate (18.8 g). The mixture was stirred for 16 hours at room temperature and concentrated in vacuo. The residue was dissolved in ethyl acetate and washed with water and brine, dried over sodium sulphate, filtered and evaporated in vacuo. The crude material was triturated by hexane, filtered and dried in vacuo to yield N—Boc—L—α-Amino—ε-caprolactam (16 g).

TLC: Rf=0.85, ethyl acetate/heptane 111 v/v on silica.

(o) Boc—norLeu(cyclo)—Gly—OMe

N—Boc—L—α-Amino—ε-caprolactam (10 g) was dissolved in dichloromethane (100 ml). At −20° C. a 1 M solution of bis (trimethylsilyl)amide in tetrahydrofuran/cyclohexane 1/1 v/v (1 equiv.) was added slowly and the mixture was stirred for 30 min. Methyl bromoacetate (4 ml) was subsequently added and the mixture was stirred for 2 hour at room temperature. Additional bis(trimethylsilyl)

amide in tetrahydrofuiran/cyclohexane 1/1 v/v was added to force the reaction to completion. The mixture was diluted by dichloromethane and washed with 0.1 N hydrochloric acid solution, water, 5% aqueous sodium hydrogencarbonate solution and brine, dried over sodium sulphate, filtered and evaporated in vacuo. The residue was purified by chromatography on silica (eluent: heptane/ethyl acetate 614 v/v) to yield 12 g Boc—norLeu(cyclo)—Gly—OMe.

TLC: Rf=0.55, ethyl acetate/heptane 6/4 v/v on silica.

(p) BenzylSO$_2$—norLeu(cyclo)—Gly—OMe

Boc—norLeu(cyclo)—Gly—OMe (3 g) was dissolved in TFA/dichloromethane 1/1 v/v (30 ml) and stirred for 1 hour at room temperature. The reaction mixture was evaporated in vacuo. The crude amine was dissolved in dichloromethane (25 ml) and a solution of benylsulphonyl-chloride (2.25 g) in dichloromethane (10 ml) was added slowly at 0° C. Triethylamine was added to keep the pH at 8 during the reaction. The mixture was stirred for 1 hour at room temperature, whereafter the mixture was concentrated in vacuo. The residue was dissolved in ethyl acetate and washed with 5% sodium hydrogencarbonate solution, water and brine, dried over sodium sulphate, filtered and evaporated in vacuo. The residue was purified by chromatography on silica (eluent: dichloromethane/ethyl acetate 95/5 v/v. to yield benylSO$_2$—norLeu(cyclo)—Gly—OMe (3.9 g)

TLC: Rf=0.40, dichloromethanelethyl acetate 9/1 v/v on silica.

(q) BenzylSO$_2$—norLeu(cyclo)—Gly—OH

A solution of benzylSO$_2$—norLeu(cyclo)—Gly—OMe (3.9 g) in 100 ml of dioxane/water 9/1 was treated with sufficient 1N sodium hydroxide to keep the pH at 13 for 2 hours at room temperature. After acidification, the mixture was poured into water and extracted with dichloromethane. The organic layer was washed with water and dried on sodium sulphate The filtrate was evaporated and yielded 3.6 g of the title compound.

TLC: Rf=0.60, ethyl acetate/pyridinelacetic acid/water 63/20/6/11 v/v/v/v on silica.

(r) BenzylSO$_2$—norLeu(cyclo)—Gly—S—PpaΨ[COCO]—OH

The DCCI/HOBt-coupling between benzylSO$_2$—norLeu(cyclo)—Gly—OH and H—S—Ppa(Boc)Ψ[CHOHCO]—OMe.HCl, saponification, Dess-Martin oxidation, deprotection and purification were done according to the procedures described in example 1.

R$_t$ (LC): 27.41 min. 20% A/80% B to20% A/20% B/60% C in 40 min.

EXAMPLE 13

1-Piq—Pro—PpaΨ[COCO]—OH

N—(Cbz)-1-Piq—OH

N—(Cbz)-1-Piq—OH has been synthesised as described in EP0643073, example 1.

TLC: Rf=0.85, ethyl acetatelpyridine/acetic acid/water 63/20/6/11 vlv/v/v on silica.

(a) N-(Cbz)-1-Piq—Pro—OtBu

To a cold solution (0° C.) of N—(Cbz)-1-Piq—OH (500 mg) in N,N-dimethylformamide (5 ml) were successively added DCCI (342 mg), HOBT (319 mg), H—Pro—OtBu. (270 mg) and triethylamine (0.55 ml). The reaction mixture was stirred at 0° C. for 1 hour and then kept at room temperature overnight. The reaction mixture was cooled to −20° C. and the DCU (1,3-dicyclohexylurea) was removed by filtration. The filtrate was concentrated in vacuo and the residue was dissolved in ethyl acetate. This solution was washed successively with 5% aqueous sodium hydrogen-carbonate solution, 3% aqueous citric acid solution, water and brine, dried over sodium sulphate and concentrated in vacuo. The residue was purified by chromatography on silica (eluent: heptane/ethyl acetate 4/1 v/v) to yield N—(Cbz)-1-Piq—Pro—OtBu (634 mg).

TLC: Rf=0.90, ethyl acetate/pyridine/acetic acid/water 63/20/6/11 v/v/v/v on silica.

(b) N—(Cbz)-1-Piq—Pro—OH

N—(Cbz)-1-Piq—Pro—O—t—Bu (600 mg) was stirred in a mixture of dichloromethane (1 ml), trifluoroacetic acid (3 ml), anisole (0.15 ml) for 1 hour at room temperature. The reaction mixture was concentrated in vacuo at low temperature and the residue was dissolved in water at pH of 9.5. The aqueous phase was washed with diethyl ether, whereafter the aqueous layer was acidified to pH 2.5 by 2 M hydrochloric acid solution. The aqueous layer was ettracted with ethyl acetate and the organic phase was washed with brine, dried over sodium sulphate and concentrated in vacuo to yield N—(Cbz)-1-Piq—Pro—OH (588 mg).

TLC: Rf=0.54, ethyl acetate/pyridinelacetic acid/water 60/3/1/2 v/v/v/v on silica (c) 1-Piq—Pro—PpaΨ[COCO]—OH The DCCI/HOBt-coupling between N—(Cbz)-1-Piq—Pro—OH and H—Ppa(Boc)Ψ[CHOHCO]—OMe.HCl, saponification, Dess-Martin oxidation, deprotection and purification were done according to the procedures described in example 1. The title compound was isolated as a diastereomeric mixture.

R$_t$ (LC): 19.8 and 20.31 min. 20% A/80% B to 20% A/20% B/60% C in 40 min.

EXAMPLE 14

H—D—Phe—Pro—PpaΨ[COCO]—OH

Boc—D—Phe—Pro—OH was prepared according to a similar procedure as described in example 1. The DCCI/HOBt-coupling between Boc—D—Phe—Pro—OH and H—Ppa(Boc)Ψ[CHOHCO]—OMe.HCl, saponification, Dess-Martin oxidation, deprotection and purification were done according to the procedures described in example 1 to give a diastereomeric mixture.

R$_t$ (LC): 16.24 and 16.90 min. 20% A/80% B to 20% A/20% B/60% C in 40 min.

EXAMPLE 15

3,3-Diphenyipropionyl—Pro—PpaΨ[COCO]—OH 3,3-Diphenylpropionyl—Pro—OH was prepared according to a similar procedure as described in example 1. The DCCI/HOBt-coupling between 3,3-Diphenylpropionyl—Pro—OH and H—Ppa(Boc)Ψ[CHOHCO]—OMe.HCl, saponification, Dess-Martin oxidation, deprotection and purification were done according to the procedures described in example 1 to give a diastereomeric mixture.

R$_t$ (LC): 36.60min. 20% A/80% B to 20% A/20% B/60% C in 40 min.

EXAMPLE 16

H—(N—Me)—D—Cha—Pro—PpaΨ[COCO]—OH (a) Boc—D—Cha—OMe

Boc—D—Cha—OH (20 g) was dissolved in dichloromethanetmethanol 9/1 vlv (400 ml). 2-(1H-benzotriazol-1-yl)-1,1,3,3-tetramethyluronium tetrafluoroborate (22.7 g) was added and the solution adjusted to pH 8 by addition of triethylaraine (10 ml). The reaction mixture was stirred for 16 hours at room temperature. The mixture was washed successively with cold 1 N hydrochloric acid solution, water, 5% sodium hydrogencarbonate, and water and dried over sodium sulphate. The filtrate was evaporated and the residue was chromatographed on silica gel luting with ethyl acetate/heptane 213 v/v as eluent. The fractions containing Boc—D—Cha—OMe were pooled and evaporated. Yidd: 19.38 g TLC: Rf=0.90, silica gel, ethyl acetate/heptane 3/1 v/v.
(b) Boc—(N—Me)—D—Cha—OMe Boc—D—Cha—OMe (19.35 g) was dissolved in 200 ml dry N,N-dimethylfonwnide under nitrogen atmosphere. Methyliodide (4.22 ml) was added and the mixture was cooled to 0° C. 2.71 g sodium hydride (60% dispersion in oil) was added and the reaction mixture was stirred for 3 hours at room temperature. The mixture was partially concentrated, ethyl acetate was added and the organic layer was washed with 0.1M hydrochloric acid, water, 5% sodium hydrogencarbonate solution and brine, dried over sodium sulphate and concentrated. Yield: 21.07 g.

TLC: Rf=0.55, silica gel, ethyl acetateiheptane 3/7 v/v.
(c) H—(N—Me)—D—Cha—Pro—PpaΨ[COCO]—OH Boc—(N—Me)—D—Cha—Pro—OH was prepared according to a similar procedure as described in example 1. The DCCI/HOBt-coupling between Boc—(N—Me)—D—Cha—Pro—OH and H—PpaΨ[CHOHCO]—OMe.HCl, saponification, Dess-Martin oxidation, deprotection and purification were done according to the procedures described in example 1. The title compound was isolated as a diastereomeric mixture.

$R_t$ (LC): 23.14 min. 20% A/80% B to 20% A/20% B/60% C in 40 min.

EXAMPLE 17
H—(N—Me)—D—Phe—Pro—PpaΨ[COCO]—OH

Boc—(N—Me)—D—Phe—Pro—OH was prepared according to similar procedures as described in example 1. The DCCI/HOBtcoupling between Boc—(N—Me)—D—Phe—Pro—OH and H—Ppa(Boc)Ψ[CHOHCO]—OMe.HCl, saponification, Dess-Martin oxidation, deprotection and purification were done according to the procedures described in example 1 to yield the title compound as a diastereomeric mixture.

$R_t$ (LC): 16.26/16.90 min. 20% A/80% B to 20% A/20% B/60% C in 40 nmin.

EXAMPLE 18
EthylSO$_2$—D—Cha—Pro—PpaΨ[COCO]—OH
Boc—D—Cha—Pro—OPac(OPac=Phenacyl ester)

Boc—D—Cha—Pro—OPac was prepared according a similar manner as described in example 1 using Boc—D—Cha—OH and H—Pro—OPac.

TLC: Rf=0.5, dichloromethane/methanol 95/5 v/v on silica
(a) EthylSO$_2$—D—Cha—Pro—OPac Boc—D—Cha—Pro—OPac (3.8 g) was dissolved in TFA/dichloromethane 1/1 v/v (25 ml) and stirred for 30 minutes at room temperature. The reaction mixture was evaporated in vacuo. The crude amine was dissolved in dichloromethane (50 ml) and ethanesulphonyl chloride (0.8 ml) was added at −78° C. Triethylamine was added to keep the pH at 8 during the reaction. The mixture was stirred for 3 hours at 0° C., whereafter water (25 ml) was added. After additional stirring for 30 minutes at room temperature, the reaction mixture was concentrated in vacuo. The residue was dissolved in diethyl ether and washed with 1 N hydrochloric acid solution, water, 5% sodium hydrogencarbonate solution and brine, dried over sodium sulphate, filtered and evaporated in vacuo. Trituration of the crude material with methanol yielded ethylSO$_2$—D—Cha—Pro—OPac (3.0 g).

TLC: Rf=0.6, dichloromethane/methanol 95/5 v/v on silica.
(b) EthylSO$_2$—D—Cha—Pro—OH To a solution of ethylSO$_2$—D—Cha—Pro—OPac (10 g) in tetrahydrofuran (250 ml) was added 1 M solution of tetrabutylammonium fluoride in tetrahydrofuran (84 ml).

The reaction mixture was stirred for 30 minutes at room temperature and poured into water (1 l). The aqueous solution was extracted with ethyl acetate. The combined organic layers were successively wasad with 1N hydrochloric acid solution and water, dried over sodium sulphate and concentrated in vacuo. The residue was purified by crystallisation from ethyl acetate/diisopropylether to yield ethylSO$_2$—D—Cha—Pro—OH (6.0 g).

TLC: Rf=0.2, ethyl acetate/pyridine/acetic acid/water 163/20/6/11 v/v/v/v on silica.
(c) EthylSO$_2$—D—Cha—Pro—PpaΨ[COCO]—OH The DCCI/HOBt-coupling between ethylSO$_2$—D—Cha—Pro—OH and H—Ppa(Boc)Ψ[CHOHCO]—OMe.HCl, saponification, Dess-Martin oxidation, deprotection and purification were done according to the procedures described in example 1 to yield the title compound as a diastereomeric mixture.

$R_t$ (LC): 35.90 min. 20% A/80% B to 20% A/20% B/60% C in 40 min.

EXAMPLE 19
N—Me—D—Cha—Azt—Ppa—(2-thiazolyl)
(a) H—Azt—OBzl.HCl

N—Boc—Azt—OH (4.60 g) was dissolved in dichloromethane (50 ml) and treated with beneyl alcohol (2.47 g), 2-(IH-benztriazole-1-yl)-1,1,3,3-tetramethyluronium tetrafluoroborate (7.40 g) and triethylamine (6.3 ml) and stirred for 1 hour at room temperature. The reaction mixture was diluted with 1 N hydrochloric acid, whereafter the organic phase was separated, washed with water, 5% sodium hydrogencarbonate and brine. Filtration, followed by evaporation in vacuo afforded the crude product, which was purified by silica gel chromatography in heptane/ethyl acetate 3/1 v/v to give N—Boc—Azt—OBzl (6.0 g). Subsequent removal of the Boc protecting group in a 3 M hydrochloric acid solution in dioxane (60 ml) for 1 hour at room temperature afforded, after evaporation to dryness, the desired product (5.26 g)

TLC: Rf=0.50, silica gel, ethyl acetate/pyridine/acetic acid/water 63/20/6/11 v/v/v/v.
(b) Boc—(N—Me—Cha—Azt—OH 1.5 g Boc—(N—Me)—D—Cha—OH (see example 58) and 1.5 g H—Azt—OBzl.HCl were coupled according to the methods as described in example 1 for the synthesis of the dipeptide. Hydrogenolysis (see example 1) of the benzyl ester afforded 1.22 g Boc—(N—Me)—D—Cha—Azt—OH TLC: Rf=0.50, silica gel, ethyl acetate/pyridine/acetic acid/water =63/20/6/11 v/v/v/v.
(c) N—Me—D—Cha—Azt—Ppa—(2-thiazolyl).

Coupling of Boc—(N—Me)—D—Cha—Azt—OH (370 mg) with H—Ppa(Teoc)-(2-thiazolyl).TsOH (610 mg) as described in example 48 yielded Boc—(N—Me)—D—Cha—Azt—Ppa(Teoc)-(2-thazoy) (684 mg), after silica gel purification in dichloromethane/methanol 95/5 v/v. Subsequent removal of the protecting groups (see example 48) gave after HPLC purification the two separated diastereomers.

Yield:76 mg. $R_t$ (LC): 26.9 min , 20% A, 80% B to 20% A, 20% B and 60% C in 40 min.

Yield: 76 mg. $R_t$ (LC): 30.3 min, 20% A, 80% B to 20% A, 20% B and 60% C in 40 min.

EXAMPLE 20
H—D—Hpl—Pro—PpaΨ[COCO]—OH
(a) H—D—Hpl—OMe

H—D—Cha—OH (1.0 g) was dissolved in a mixture of 1 N hydrochloric acid (4.8 ml), water (19.4 ml) and acetic acid (9.7 ml). At 0° C. a solution of sodium nitrite (3.4 g) in water (5.8 ml) was added slowly and the mixture was stirred overnight at room temperature. Hydrochloric acid, 37%, (4.8 ml) was subsequently added and the mixture was stirred for 15 min at room temperature. The reaction mixture was concentrated and the residue was dissolved in ether/acetone. After filtration, the solution was concentrated in vacuo and the crude material was stirred in methanol (25 ml) for 18 hours The pH was 1.5. The reaction mixture was evaporated to dryness and the residue was purified by chromatography on silica (eluent: toluenetmethanol 97/3 v/v. to yield H—D—Hpl—OMe (612 mg)

TLC: Rf=0.9, ethyl acetate/pyridinetacetic acid/water 163/20/6/11 v/v/v/v on silica.

(b) THP—D—Hpl—OMe
(THP=tetrahydropyran)

To a stirred solution of H—D—Hpl—OMe(450 mg) in dichloromethane (2 ml) was successively added 3,4dihydro2H-pyran (0.29 ml) and pyridinium ptoluenesulfonate (60 mg). The mixture was stirred for 6 hours at room temperature and diluted with ether. This mixture was washed with brine, dried over sodium slphate, filtered and evaporated in vacuo. The crude material was purified by chromatography on silica (eluent: ethyl acetate/heptane 1/4 v/v) to yield THP—D—Hpl—OMe (498 mg).

TLC: Rf=0.64, ethyl acetate/heptane 1/2 v/v on silica.

(c) THP—D—Hpl—OH

A solution of THP—D—Hpl—OMe (10.3 g) in dioxane/water 9/1 v/v (200 ml) at room temperature was treated with sufficient IN sodium hydroxide to keep the pH at 12 for 18 hours. After acidification, the mixture was poured into water (500 ml) and extracted with dichloromethane. The organic layer was washed with water and dried on sodium sulphate The filtrate was evaporated and yielded 6.6 g of the title compound.

TLC: Rf=0.78, ethyl acetate/pyridine/acetic acid/water 163/20/6/11 v/v/v/v on silica.

(d) THP—D—Hpl—Pro—OH

To a solution of THP—D—Hpl—OH (5.87 g) in acetonitrile (75 ml) was successively added EDCI (1-(3-dimethylaminopropyl)-3-ethylcarbodiimide hydrochloride) (4.84 g) and N-hydroxy-succinimide (2.9 g). The reaction mixture was stirred at room temperature for 16 hours The mixture was concentrated in vacuo and the residue was dissolved in ethyl acetate. This solution was washed with water and brine, dried over sodium sulphate and concentrated in vacuo. The crude material was dissolved in N,N-dimethylformamide (100 ml) and added to a solution of proline.HCl (6.99 g) in N,N-dimethylformamidelwater, 1/1, v/v (200 ml), which was adjusted to a pH of 8.5 by sodium hydroxide. After stirring overnight the reaction mixture was concentrated in vacuo and the residue was dissolved in water. This aqueous solution was adjusted to pH 2.5 at 0° C., followed by extraction with ethyl acetate. The combined organic layers were successively washed with water and brine, dried over sodium sulphate and concentrated in vacuo. The crude material was purified by chromatography on silica (eluent: ethyl acetatelmethanol, 8/2 to 6,4 v/v) to yield THP—D—Hpl—Pro—OH (6.75 g).

TLC: Rf=0.52, ethyl acetatelpyridine/acetic acid/water 163/20/6/11 v/v/v/v on silica.

(e) H—D—Hpl—Pro—PpaΨ[COCO]—OH

The DCCI/HOBt-coupling between THP—D—Hpl—Pro—OH and H—Ppa(Boc)Ψ[CHOHCO]—OMe.HCl, saponification, Dess-Martin oxidation, deprotection and purification were done according to the procedures described in example 1 to give a diastereomeric minure.

$R_t$ (LC): 31.05 min.20% A/80% B to 20% A/20% B/60% C in 40 min.

EXAMPIE 21

3,3-Diphenylpropionyl—Pro—PpaΨ[COCO]—OMe 3,3-Diphenylpropionyl—Pro—OH was prepared according to similar procedures as described in example 1. The DCCI/HOBt-coupling between 3,3-Diphenylpropionyl—Pro—OH and H—Ppa(Boc)Ψ[CHOHCO]—OMe.HCl, DessMartin oxidation, deprotection and purification were done according to the procedures described in example 1 to yield the title compound as a diastereomeric mixture.

$R_t$ (LC): 21.7 min. 20% A/60% B/20% C to 20% A/80% C in 30 min.

EXAMPLE 22

EthylSO$_2$—D—Cha—Pro—PpaΨ[COCO]—OMe

EthylSO$_2$—D—Cha—Pro—OH is described in example 18. The DCCI/HOBt-coupling between ethylSO$_2$—D—Cha—Pro—OH and H—Ppa(Boc)Ψ[CHOHCO]—OMe.HCl, Dess-Martin oxidation, deprotection and purification were done according to the procedures described in example 1 to give the title compound as a diastereomeric mixture.

$R_t$ (LC): 39.06 min. 20% A/80% B to 20% A/20% B/60% C in 40 min.

EXAMPLE 23

HOOC—CH$_2$—Cha—Pro—PpaΨ[COCO]—OMe

N—(t-Butyloxycarbonylmethyl)—N—Boc—D—Cha—Pro—OH is described in example 1. The DCCI/HOBt-coupfing between N—(t-butyloxycarbonylmethyl) N—Doc—D—Cha—Pro—OH and H—Ppa(Boc)Ψ[CHOHCO]—OMe.HCl, Dess-Martin oxidation, deprotection and purification were done according to the procedures described in example 1 to give a diastereomeric mixture.

$R_t$ (LC): 25.75 min. 20% A/80% B to 20% A/20% B/60% C in 40 min.

EXAMPLE 24

EthylSo$_2$—D—Cha—Pno—PpaΨ[COCO]—OEt

EthylSO$_2$—D—Cha—Pro—OH was prepared according to similar procedures as described in example 18.

(a) Cbz—PpaΨ[CHOHCO]—OEt

A solution of Cbz—Ppa(Boc)Ψ[CHOHCO]—OMe (1 g) in 50 ml of a 3 M hydrogen chloride/ethanol at −20° C. was stirred for 4 hours while raising the temperature to room temperature. The mixture was evaporated in vacuo yielding 0.9 g of the title compound as an oil.

TLC: Rf=0.85, silica gel, ethyl acetate/pyridine/acetic acid/water 63/20/6/11 v/v/v/v.

(b) Cbz—Ppa(Boc)Ψ[CHOHCO]—OEt

The pH of a solution of 0.9 g of Cbz—PpaΨ[CHOHCO]—OEt and 0.55 g of di—t-butyl dicarbonate in 10 ml of N,N-dimethylformamide was adjusted to pH 8.5 by addition of triethylamine. The mixture was stirred for 1 hour at room temperature, poured into water and extracted with ethyl acetate. The combined extracts were washed with 1 M hydrochloric acid, water, 5% sodium hydrogencarbonate-solution and water, dried over sodium sulphate and evaporated in vacuo, yielding 0.99 g. of the title compound as an oil.

TLC: Rf=0.60, silica gel, heptane/ethyl acetate 1/1 v/v.

(c) EthylSO$_2$—D—Cha—Pro—PpaΨ[COCO]—OEt

Cbz—Ppa(Boc)Ψ[CHOHCO]—OEt was hydrogenated according to example 2(q) to give H—Ppa(Boc)Ψ[CHOHCO]—OEt.HCl. The DCCI/HOBt coupling between ethylSO$_2$—D—Cha—Pro—OH and H—Ppa(Boc)Ψ[CHOHCO]—OEt.HCl, Dess-Martin oxidation, deprotection and purification were done according to the procedures described in example 1 toyield the title compound as a diastereomeric mixture.

R$_t$ (LC): 41.58 min. 20% A/80% B to 20%A/20% B/60% C in 40 min.

EXAMPLE 25
HOOC—CH$_2$—D—Cha—Pro—PpaΨ[COCO]—OEt

N—(t-Butyloxycarbonylmethyl)—N—Boc—D—Cha—Pro—OH is described in example 1. The DCCI/HOBt-coupling between N—(t-butyloxycarbonylmethyl)—N—Boc—D—Cha—Pro—OH and H—Ppa(Boc)Ψ[CHOHCO]—OEt.HCl, Dess-Martin oxidation, deprotection and purification were done according to the procedures described in example 1 to yield the title compound as a diastereomeric mixture.

R$_t$ (LC): 28.20 min. 20% A/80% B to 20% A/20% B/60% C in 40 min.

EXAMPLE 26
EthylSO$_2$—D—Phe—Pro—PpaΨ[COCO]—OEt

EthylSO$_2$—D—Phe—Pro—OH was prepared according to similar procedures as described in example 18. The DCCI/HOBt-coupling between ethylSO$_2$—D—Phe—Pro—OH and H—Ppa(Boc)Ψ[CHOHCO]—OEt.HCl, Dess-Martin oxidation, deprotection and purification were done according to the procedures described in example 1 to give a diastereomeric mixture.

R$_t$ (LC): 34.89 min. 20% A/80% B to 20% A/20% B/60% C in 40 min.

EXAMPLE 27
EthylSO$_2$—D—Cha—Pro—Ppa(Eoc)Ψ[COCO]—OEt (Eoc=ethoxycarbonyl)

(a) EthylSO$_2$—D—Cha—Pro—PpaΨ[CHOHCO]—OEt

EthylSO$_2$—D—Cha—Pro—Ppa(Boc)Ψ[CHOHCO]—OEt was prepared according to a similar manner as described in example 24. The hydroxythylester (200 mg) was treated with trifluoroacetic acid/dichloromethane 1/1 for 1 hour at room temperature yielding 210 mg of the title compound.

TLC: Rf=0.85, silica gel, ethyl acetate/pyridine/acetic acid/water 63/20/6/11 v/v/v/v.

(b) EthylSO$_2$—D—Cha—Pro—Ppa(Eoc)Ψ[CHOHCO]—OEt

The pH of a solution of 210 mg of ethylSO$_2$—D—Cha—Pro—PpaΨ[CHOHCO]—OEt and 43.6 μl ethyl chloroformate in 10 ml N,N-dimethylfornamide was adjusted to pH 8.5 by addition of triethylamine. The mixture was stirred for 1 hour at room temperature, poured into water and extracted with ethyl acetate. The combined extracts were washed with 1 M hydrochloric acid, water, 5% sodium hydrogencarbonate-solution and water, dried over sodium sulphate and evaporated in vacuo, yielding 220 mg of the title compound as an oil.

TLC: Rf=0.50, silica gel, ethyl acetate/pyridine/acetic acid/water 463/20/6/11 v/v/v/v.

(c) EthylSO$_2$—D—Cha—Pro—Ppa(Eoc)Ψ[COCO]—OEt

The Dess-Martin oxidation and purification were done according to the procedures described in example 1 to yield the title compound as a diastereomeric mixture.

R$_t$ (LC): 13.95 min. 70% B/30% C to 30% B/70% C in 40 min.

EXAMPLE 28
EthylSO$_2$—D—Cha—N-cyclopentyl—Gly—S—Ppa—(2-thiazolyl)

(a) EthylSO$_2$—D—Cha—N-cyclopentyl—Gly—OH

Boc—D—Cha—OH (2.65 g) was coupled with N-cyclopentyl—Gly—OMe.HCl (See example 2) according to the dipeptide synthesis as described in example 1, to give N—Boc—D—Cha—N-cyclopentyl—Gly—OMe (3.5 g) after silica gel purification. Subsequent removal of the Boc protective group in TFA/dichloromethane 1/1 v/v (38 ml), followed by the ethyl sulfonylation, as described in example 18, afforded ethylSO$_2$—D—Cha—N-cyclopentyl—Gly—OMe (1.4 g). Hydrolysis of the methyl ester was performed according to the procedures as described in example 2, yielding ethylSO$_2$—D—Cha—N-cyclopentyl—Gly—OH.

TLC: Rf=0.2, silica gel, dichloromethane/methanol 9/1 v/v.

(b) (2S)2-Azido3-(piperidin-4-yl)-propanoic acid

A solution of 3.7 g of (2S)-2-azido-3-[1-(t-butyloxycarbonyl)piperidin-4-yl]-propanoic acid (example 12(e)) was treated with 30 ml of 3M hydrogen chloride in ethyl acetate. The nature was stirred for 30 min. at room temperature, evaporated in vacuo and gave 3.0 g of a crystalline solid.

TLC: Rf=0.35 in ethyl acetatetpyridine/acetic acid/water 63/20/6/1i1 v/v/v/v on silica.

(c) (2S)-2-azido-3-[1-[2-trimethylsilyl)ethoxycarbonyl] piperidin-4-yl]-propanoic acid The pH of a mixture of 3.0 g of (2S)-2-azido-3-(piperidin-4-yl)-propanoic acid and 1-[2-(trimethylsilyl)ethoxycarbonyloxy]pyrrolidin-2,5-dione (TeocOSu, reference: Synthesis 1987, 346) was adjusted at pH 8.5 with triethylamine The reaction mixture was stirred for 30 min at room temperature, poured into water and extracted with ethyl acetate. The combined extracts were washed with 1 N hydrochloric acid, water, 5% sodium hydrogencarbonate, and water and dried on sodium sulphate. Evaporation in vacuo gave 4.93 g of the desired compound as an oil TLC: Rf=0.85 in ethyl acetate/pyridine/acetic acid/water 63/20/6/11 v/v/v/v on silica.

(d) (2S)-N-Methyl-N-methoxy-2-azido-3-[1-[(2-trimethylsilyl)ethoxycarbonyl]pipeindin-4-yl]-propanamide (2S)-N-Methyl-N-methoxy-2-azido-3-[1-[(2-trimethylsilylethoxycarbonyl]piperidin-4-yl]-propananide was prepared according to similar manner as described in example 12(f) using (2S)-2-azido-3-[1-[(2-trimethylsilyllethoxycarbonyl]piperidin-4-yl]propanoic acid.

TLC: Rf=0.85, silica gel, ethyl acetate/pyridine/acefic acid/water 63/20/6/11 v/v/v/v.

(e) H—S—Ppa(Teoc)—N(Me)OMe

Hydrogen was passed through a mixture of 4.9 g of (2S)-N-methyl-N-methoxy-2-azido-3-[1-[(2-trimethylsilyl) ethoxycarbonyl]piperidin-4-yl]-propanamide and 0.5 g of Pd/C (10%) in 100 ml of tetrahydrofuiran and 13.3 ml of 1 N hydrochloric acid until all starting material had disappeared. The catalyst was filtered off and the solvent removed in vacuo to yield 5.7 g of the desired compound.

TLC: Rf=0.9 in ethyl acetate/pyridinelacetic acid/water 63/20/6/11 v/v/v/v on silica.

(f) Boc—S—Ppa(Teoc)—N(Me)OMe

The pH of a solution of 4.7 g of H—S—Ppa(Teoc)—N(Me)OMe and 2.8 g of di—t-butyl dicarbonate was adjusted at pH 8.5 with triethylamine. The mixture was stirred for 1 hour at room temperature, poured into water and extracted with ethyl acetate. The combined organic layers were washed with 1N hydrochloric acid , water, 5% sodium hydrogencarbonate and water, dried on sodium sulphate and evaporated in vacuo to yield 5.2 g of the title compound as an oil.

TLC: Rf=0.85 in ethyl acetate/pyridine/acetic acid/water 63/20/6/11 v/v/v/v on silica. Chiral HPLC on a chiralpack colum Chir 11 250×4.6 in hexane/ethanol 9/1 v/v gave 91% ee.

(g) Boc—S—Ppa(Teoc)-(2-thiazolyl)

To a solution of 31.7 ml of 1.05 M n-BuLi in ether at −78° C. under nitrogen atmosphere was added 5.46 ml of 2-bromothiazole. The resulting precooled yellow solution (2.5 eq) was added via a cannula to a solution of Boc—S—Ppa(Teoc)—N(Me)OMe in 46 ml of dry tetrahydrofuran at −78° C. under nitrogen atmosphere. The reaction mixture was stirred for 30 min at −78° C. under nitrogen atmosphere, poured into 5% sodium hydrogencarbonate and extracted with ethyl acetate. The combined organic layers were washed with water, dried on sodium sulphate and evaporated in vacuo and to give 5.0 g of an oily residue. Flashchromatography in heptanejethyl acetate 7/3 v/v on silica yielded 1.7 g of the title compound.

TLC: Rf=0.75 in heptane/ethyl acetate 7/3 v/v on silica. $[\alpha]_D$=+31.9° (c=0.45 in $CHCl_3$)

(h) H—S—Ppa(Teoc)-(2-thiazolyl).TsOH

To a solution of 1.54 g of Boc—S—Ppa(Teoc)-(2-thiazolyl) in 14.2 ml of dry ether were added a solution of 0.96 g of p-toluenesulphonic acid. mono hydrate in 2.8 ad of dry ethanol. The solution was kept 1hour at 30° C. and the ether was removed. The resulting solid was washed with dry ether and gave 1.5 g of the title compound as a solid.

TLC: Rf=0.85 in dichloromethane/methanol 9/1 v/v (i)EthylSO$_2$—D—Cha—N-cyclopently—Gly—S—Ppa—(2-thiazolyl)

Coupling of ethylSO$_2$—D—Cha—N-cyclopentyl—Gly—OH (395 mg) with H—S—Ppa(Teoc)-(2-thiazolyl).TsOH, according to the methods described in example 48, afforded 400 mg of fully protected tripeptide. The Teoc group was removed (see example 48) to give 300 mg crude ethylSO$_2$—D—Cha—N-cyclopentyl—Gly—S—Ppa—(2-thiazolyl).TFA. This salt (150 mg) was purified by HPLC to yield 112 mg of the target compound.

R$_t$ (LC): 32.06 in 20% A, 60% B and 20% C to 100% C in 40 min.

EXAMPLE 29

EthylSO$_2$—D—Cha—N-cyclopentyl—Gly—S—Ppa(Eoc)-(2-thiazolyl)

EthylSO$_2$—D—Cha—N-cyclopentyl—Gly—S—Ppa—(2-thiazolyl).TFA (150 mg) (example 28) was dissolved in N,N-dimethylfonnamide (10 ml) and treated with ethyl chloroformate (38 μl) at pH≈8.5 (triethyl amine) and stirred for 2 hours at room temperature. The reaction mixture was diluted with ethyl acetate (100 ml), washed with 1N hydrochloric acid, water, 5% sodium hydrogencarbonate and water. The organic phase was dried over sodium sulphate, filtered and evaporated to dryness to yield ethylSO$_2$—D—Cha—N-cyclopentyl—Gly—S—Ppa(Eoc)-(2-thiazolyl) (100 mg)

TLC: Rf=0.45, silica, dichloromethane/methanol 9/1 v/v.

EXAMPLE 30

HOOC—CH$_2$—D—Cha—Pro—PpaΨ[COCO]—NH$_2$ (a) N—(t-Butyloxycarbonylmethyl)—N—Boc—D—Cha—Pro—Ppa(Boc)Ψ[CHOHCO]—OH N—(t-Butyloxycarbonylmethy)—N—Boc—D—Cha—Pro—OH is described in example 1. The DCCI/HOBt coupling between N—(t-butyloxycabonylmethyl)—N—Boc—D—Cha—Pro—OH and H—Ppa(Boc)Ψ[CHOHCO]—OMe.HCl, and the saponification were done according to the procedure descnbed in example 1.

TLC: Rf=0.80, silica gel, ethyl acetate/pyridinelacetic acid/water 63/20/6/11 v/v/v/v.

(b) N—(t-Butyloxycarbonylmethyl)—N—Boc—D—Cha—Pro—Ppa(Boc)Ψ[CHOHCO]—NH$_2$

N—(t-Butyloxycarbonylmethyl)—N—Boc—D—Cha—Pro—Ppa(Boc)Ψ[CHOHCO]—OH (400 mg) was dissolved in N,N-dimethylforamide (12 ml). The solution was cooled on a iowater bath and 91.3 mg of HOBT, 91.3 μl of N-methylmorpholine, 50.5 mg of ammoniumchloride and 102 mg of EDCI were subsequently added. The reaction mixture was stirred for 16 hours at room temperature. The mixture was poured out in a 1M hydrochloric acid and extracted with ethyl acetate. The combined extracts were washed with water, 5% sodium hydrogencarbonate solution, water, dried over sodium sulphate and evaporated in vacuo to yield 400 mg of the title compound.

TLC : Rf:=0.25, silica gel, ethyl acetatelpyridine/acetic acid/water 63/20/6/11 v/v/v/v.

(c) HOOC—CH$_2$—D—Cha—Pro—PpaΨ[COCO]—NH$_2$

The Dess-Martin oxidation, the deprotection and purification were done according to the procedure described in example 1. Yield: 94.2 mg of the title compound as a diastereomeric mixture.

R$_t$ (LC): 22.97 min.20% A/80% B to 20% A/20% B/60% C in 40 min.

EXAMPLE 31

HOOC—CH$_2$—D—Cha—Pro—PpaΨ[COCO]—NHMe

N—(t-butyloxyarbonylmethyl)—N—Boc—D—Cha—Pro—Ppa(Boc)Ψ[CHOHCO]—NHMe was prepared according to example 30 using methylamine. The Dess-Martin oxidation, the deprotection and purification were done according to the procedure described in example 1 to give the title compound as a diastereomeric mixture.

R$_t$ (LC): 24.22 and 24.99 min. 20% A 80% B to 20% A/20% B 60% C in 40 min.

EXAMPLE 32

HOOC—CH—D—Cha—Pro—PpaΨ[COCO]-(1-azetidine)

N—(t-Butyloxyconyimethyl)—N—Boc—D—Cha—Pro—Ppa(Boc)Ψ[CHOHCO]-(1-azetidine) was prepared according to example 30 using azetidine.HCl. The Dess-Martin oxidation, the deprotection and purification were done according to the procedure described in example 1 to give a diastereomeric mixture.

R$_t$ (LC): 28.05 and 28.34 min. 20% A/80% B to 20% A/201% B/60% C in 40 min.

EXAMPLE 33

HOOC—CH$_2$—D—Cha—Pre—PpaΨ[COCO]—(NH—(CH$_2$)$_2$-Phenyl)

N—(t-Butyloxycarbonylmethyl)—N—Boc—D—Cha—Pro—Ppa(Boc)Ψ[CHOHCO]—(N—(CH$_2$)$_2$-Phenyl) was prepared according to example 30 using 2-(phenyl) ethylamine. The Dess-Martin oxidation, the deprotection and purification were done according to the procedure described in example 1 to give the title compound as a diastereomeric mixture.

R$_t$ (LC): 38.82 min. 20% A/80% B to 20% A/20% B/60% C in 40 min.

EXAMPLE 34

HOOC—CH$_2$—D—Cha—Pro—PpaΨ[COCO]—(NH—CH$_2$Phenyl)

N—(t-Butyloxycarbonylmethyl)—N—Boc—D—Cha—Pro—Ppa(Boc)Ψ[CHOHCO]—(NH—CH$_2$Phenyl) was prepared according to example 30 using benzylamine. The Dess-Martin oxidation, the deprotection and purification were done according to the procedure described in example 1 to yield the title compound as a diastereomeric mixture.

R$_t$(LC): 36.46 min. 20% A/80% B to 20% A/20% B/60% C in 40 min.

EXAMPLE 35
EthylSO$_2$—D—Cha—Pr0—PpaΨ[COCO]—NH$_2$

EthylSO$_2$—D—Cha—Pro—OH is described in example 18. The DCCI/HOBt-coupling between ethySO$_2$—D—Cha—Pro—OH and H—Ppa(Boc)Ψ[CHOHCO]—OMe.HCl, saponification and EDCI-coupling with ammoniumchloride were done according to the procedures described in example 30. Dess-Martin oxidation, deprotection and purification were done according to the procedures described in example 1 to give a diastereomeric mixture.

R$_t$ (LC): 36.7 0 min. 20% A/80% B to 20% A/20% B/60% C in 40 min.

EXAMPLE 36
EthylSO$_2$—D—Cha—Pro—PpaΨ[COCO]-(NH—CH$_2$Phenyl)

EthylSO$_2$—D—Cha—Pro—OH was prepared as described in example 18. The DCCI/HOBt-coupling between ethylSO$_2$—D—Cha—Pro—OH and H—Ppa(Boc)Ψ[CHOHCO]—OMe.HCl, saponification and EDCI-coupling with benylamine were done according to the procedures described in example 30. Dess-Martin oxidation, deprotection and purification were done according to the procedures described in example 1 to give the title compound as a diastereomeric mixture.

R$_t$ (LC): 28.76 and 29.1 min.20% A/60% B/20% C to 20% A/80% C in 30 min.

EXAMPLE 37
EthylSO$_2$—D—Cha—Pro—PpaΨ[COCO]—NMe$_2$

EthylSO$_2$—D—Cha—Pro—OH was prepared as described in example 18. The DCCI/HOBt-coupling between ethylSO$_2$—D—Cha—Pro—OH and H—Ppa(Boc)Ψ[CHOHCO]—OMe.HCl, saponification and EDCI-coupling with dimethylamine were done according to the procedures described in example 30. Dess-Martin oxidation, deprotection and purification were done according to the procedures descnbed in example 1 to give the title compound as two diastereomers.

A: R$_t$ (LC): 41.96 min. 20% A/80% B to 20% A/20% B/60% C in 40 min.

B: R$_t$ (LC): 43.49 min. 20% A/80% B to 20% A/20% B/60% C in 40 min

EXAMPLE 38
EthylSO$_x$—D—Phe—Pr0—Ψ[COCO]—NH$_2$

EthylSO$_2$D—Phe—Pro—OH was prepared according to similar procedures as described in example 18. The DCCI/HOBt-coupling between ethylSO$_2$—D—Phe—Pro—OH and H—Ppa(Boc)Ψ[CHOHCO]—OMe.HCl, saponification and EDCI-coupling with ammoniumchloride were done according to the procedures described in example 30. Dess-Martin oxidation, deprotection and purification were done according to the procedures descried in example 1 to give the title compound as a diastereomeric mixture.

R$_t$ (LC): 28.81 and29.25 min. 20% A/80% B to20% A/20% B/60% C in 40 min.

EXAMPLE 39
HOOC—CH$_2$—p—Cl—D—Phe—Pro—PpaΨ[COCO]—NH$_2$

N—(t-Butyloxycarbonylmethyl)—N—Boc—p—Cl—D—Phe—Pro—OH was prepared as described in example 5. The DCCI/HOBt-coupling between N—(t-butyloxycarbonylmethyl)—N—Boc—p—Cl—D—Phe—Pro—OH and H—Ppa(Boc)Ψ[CHOHCO]—OMe.HCl, saponification and EDCI-coupling with ammoniumchloride were done according to the procedures described in example 30. Dess-Martin oxidation, deprotection and purification were done according to the procedures descrbed in example 1 to give the title compound as a diastereomeric mixture.

R$_t$ (LC): 23.35 min. 20% A/80% B to 20% A/20% B/60% C in 40 min.

EXAMPLE 40
HOOC—CH$_2$—p—Cl—D—Phe—Pro—PpaΨ[COCO]—(NH—CH$_2$Phenyl)

N—(t-Butyloxycarbonylmethyl)—N—Boc—p—Cl—D—Phe—Pro—OH was prepared as descnied in example 5. The DCCI/HOBt coupiing between N—(t-butyloxyconyhnethyl)—N—Boc—p—Cl—D—Phe—Pro—OH and H—Ppa(Boc)Ψ[CHOHCO]—OMe.HCl, saponification and EDCI-coupling with benzylamine were done according to the procedures described in example 30. Dess-Martin oxidation, deprotection and purification were done according to the procedures described in example 1 to give two diastereomers.

A: R$_t$ (LC): 19.29 min. 20% A/60% B/20% C to 20% A/80% C in 30 min.

B: R$_t$ (LC): 37.61 min. 20% A/80% B to 20% A/20% B/60% C in 40 min.

EXAMPLE 41
[1-Oxo2-[3(phenylmethylsulphonylamine)-2-oxo-2H-pyridin-1-yl]ethyl]-PpaΨ[COCO]—(NH—CH$_2$Phenyl)

(a) [3-(Phenylmethylsulphonylamino)2-oxo-2H-pyridin-1-yl]-acetic acid (3-amino-2-oxo-2H-pyridin-1-yl)acetic acid ethyl ester is described in J. Med. Chem., 1996, 37, 3090–3099. Subsequent sulphonylation and saponification is performed according example 12.

TLC: Rf:=0.4, silica gel, ethyl acetate/pyridinetacetic acid/water 63/20/6/11 v/v/v/v.

(b) BenzylSO$_2$-3-NH$_2$- 1-carboxymethylpyridin-2-one-PpaΨ[COCO]—(NH—CH$_2$Phenyl)

The coupling between benzylSO$_2$-3-NH$_2$-1-carboxymethylpyridin-2-one and H—Ppa(Boc)Ψ[CHOHCO]—OMe.HCl (see example 1), the saponification, the amide-coupling, the Dess-Martin oxidation, the deprotection and the purification were done according to the procedures as described in example 34 to give two diastereomers A and B.

A: R$_t$ (LC): 21.6 min, 20% A, 60% B and 20% C to 100% C in 40 min.

B: R$_t$ (LC): 22.8 min, 20% A, 60% B and 20% C to 100% C in 40 min.

EXAMPLE 42
BenzylSO$_2$—norLeu(cyclo)—Gly—S—PpaΨ[COCO]—(NH—CH$_2$Phenyl)

BenzylSO$_2$-norLeu(cyclo)—Gly—OH was prepared according to similar procedures as described in example 12. The DCCI/HOBt-coupling between benylSO$_2$—norLeu (cyclo)—Gyl—OH and H—S—Ppa(Boc)Ψ[CHOHCO]—OMe.HCl (example 12(m)), saponification and EDCI-coupling with benzylanine were done according to the procedures described in example 30. Dess-Martin oxidation, deprotection and purification were done according to the procedures described in example 1.

R$_t$ (LC): 23.46 min. 20% A/60% B/20% C to 20% A/80% C in 30 min.

EXAMPLE 43
HOOC—CH$_2$—D—Cha—Pro—Ppa—(2-benzothiazolyl)

(a) Boc—Ppa(Cbz)—OMe

Boc—Ppa(Cbz)—OMe was prepared from Boc—Ppa (Cbz)—OH (example 45) according a similar procedure as described in example 1(m).

(b) Boc—Ppa(Cbz)-(2-benzothiazolyl)

To a cold (−30° C.), stirred solution of n-BuLi in hexane (3.9 ml; 1.3M), was added, dropwise, a solution of benzothiazole (675 mg) in tetrahydrofuiran (25 ml) The solution was stirred at −30° C. for 15 min. whereafter it was added slowly to a solution of Boc—Ppa(Cbz)—OMe (1.0 g) in dry tetrahydrofuiran (25 ml) at −40° C. The mixture was stirred at −20° C. for 2 hours, then 5% aqueous sodium hydrogencarbonate was added. The mixture was allowed to warm to room temperature and the layers were separated. The aqueous layer was extracted with ethyl acetate. The combined organic layers were washed with water, dried over sodium sulphate, filtered and evaporated yielding 1.83 g of an oil The residue was purified by chromatography on silica (eluent: heptanelethyl acetate 1/2, v/v) to yield the title compound (230 mg).

TLC: Rf=0.35, silica gel, heptanelethyl acetate 1/2 v/v.

(c) N—(t-Butyloxycarbonylmethyl)(Boc)—D—Cha—Pro—Ppa(Cbz)-(2-benzothiazolyl)

The deprotection of Boc—Ppa(Cbz)-(2-benzothiazole) and the coupling to N—(t-Butyloxycarbonylmethyl)(Boc)—D—Cha-Pro—OH was performed according to the procedure described in example 45. Purification by chromatography on silica gel eluting with a gradient of heptanelethyl acetate 1/1 v/v to heptane/ethyl acetate 1/2 v/v yielded 200 mg of the title compound.

TLC: Rf=0.5, silica gel, heptanetethyl acetate 1/2 v/v.

(d) HOOC—CH$_2$—D—Cha—Pro—Ppa—(2 benzothiazolyl)

To a nixture of 6 ml of trifluoroacetic acid and 0.6 ml of thioanisole was added at room temperature 0.45 g of N—(t btyloxycarbonylmethyl)(Boc)—D—Cha—Pro—Ppa(Cbz)-(2-benzothiazolyl). After 4 hours the reaction minxtre was conentrated and the residue dissolved in water. The aqueous phase was washed with diethyl ether and concentrated in vacio. The crude material was purified on a preparatieve HPLC Deltapack C18 15 μm 100 Å column using a gradient elution system of 20% A/80% B/to 20% A/35% B/45% C over 45 min at a flow rate of 50 mlmin to give the title compound as two diastereomers.

Yield: 197 mg. Rt (LC): 38.70 min, 20% A/80% B to 20% A/20% B/60% C in 40 min.

Yield: 151 mg. Rt (LC): 41.75 min, 20% A/80% B to 20% A/20% B/60% C in 40 min.

EXAMPLE 44

HOOC—CH$_2$—D—Cha—Pro—Ppa—(2-oxazolyl)

(a) 1-[[2-(trimethylsilyl)ethocylcarbonyl]-4-[2-(t-butyloxycarbonylamino)-3-hydroxy-3-(oxazol-2-yl)propyl]piperidine To a solution of 3.03 g of Boc—Ppa(Teoc)N(Me)OMe (example 48) in 50 ml of dichloromethane at −78° C. under a nitrogen atmosphere was added 20 ml of 1 M diisobutylaluminiumhydride solution in hexane. After one hour the cooling bath was removed, 100 ml of 0.25 M hydrochloric acid and additional dichloromethane were immediately added, and after 5 min the resulting suspension was filtered. Brine was added to the filtrate, the organic layer was separated, dried (sodium sulphate) and concentrated to give 2.36 g of Boc—Ppa(Teoc)—H as an oil. This aldehyde (2.36 g) and 1.86 g of 2-(trimethylsilyl)oxazole (Edwards, P. D., Wolanin, D. J., Andisik D. W., and Davis W., J. Med. Chem. 38, 76 (1995)) were mixed and heated at 50° C. for 3 hours. Then the reaction mixture was allowed to cool to room temperature and after three days the reaction mixture was concentrated. The residue was dissolved in 10 ml of tetrahydrofuran and 1 ml of 1 N hydrochloric acid. After 1 hour at room temperature ethyl acetate and brine were added and the organic layer was separated. The aqueous layer was extracted three times with ethyl acetate and the combined organic layers were dried (sodium sulphate) and concentrated. The hydrolysis was not complete and the residue was again dissolved in 10 ml of tetrahydrofuiran and 1 ml of 1 N hydrochloric acid. After one hour at room temperature ethyl acetate and brine were added and the organic layer was separated. The aqueous layer was extracted three times with ethyl acetate and the combined organic layers were dried (sodium sulphate) and concentrated. Purification by column chromatography on silica gel eluting with ethyl acetate/heptane 3/2 v/v yielded 0.70 g of the title compound.

TLC: Rf=0.2, silica gel, ethyl acetatetheptane 1/1 v/v.

(b) Boc—Ppa(Teoc)-(2-oxazolyl)

To a solution of 0.70 g of 1-[2-(trimethylsilyl)ethoxy]carbonyl]-4-[2-(t-butyloxylcartonylamino)-3-hydroxy-3-(oxazol-2-yl)propyl]piperidine in 10 ml of dichloromethane was added 0.6 g of Dess-Martin reagent. After one hour stirring at room temperature 50 ml of aqueous 5% sodium thiosulphate was added and the mixture was stirred for 45 min at room temperature. The organic layer was separated, washed with water, aqueous 5% sodium hydrogencarbonate and brine, dried over sodium sulphate and concentrated. Purification by chromatography on silica gel eluting with heptane/ethyl acetate 3/2 v/v yielded 455 mg of the title compound.

TLC: Rf=0.5, silica gel, heptane/ethyl acetate 1/1 v/v.

(c) N—(t-Butyloxycarbonylmethyl)—N—Boc—D—Cha—Pro—Ppa(Teoc)-(2-oxazolyl)

To a solution of 477 mg of Boc—Ppa(Teoc)-(2-oxazolyl) in 12 ml of diethyl ether and 2 ml ethanol was added 213 mg of p-toluenesulfonic acid mono hydrate and the ether was removed under reduced pressure at 30° C. The oily residue was heated at 60° C. for 20 min, then the ethanol was removed under reduced pressure and the residue was dried in vacuo to yield 0.5 g of H—Ppa(Teoc)-(2-oxazolyl).TsOH. To a solution of 0.29 g of N—(t-butyloxycarbonylmethyl)—N—Boc—D—Cha—Pro—OH (described in example 1) in 10 ml N,N-dimethyforrnmide under a nitrogen atmosphere at −20° C. was added 0.078 ml isobutyl chloroformate and 0.208 ml N,N-diisopropylethylamiie. After 30 min a solution of 0.25 g H—Ppa(Teoc)-(2-oxazolyl).TsOH in N,N-dimethylfonnamide and 0.050 ml N,N-diisopropylethylanine was added and the reaction niuxture was allowed to wann to room temperature. After two hours the reaction mixture was concentrated under reduced pressure. The residue was dissolved in ethyl acetate, washed with a 5% sodium hydrogencarbonate solution and brine, dried (sodium sulphate) and concentrated. Purification by chromatography on silica gel eluting with a gradient of heptane/ethyl acetate 1/1 v/v to heptane/ethyl acetate 1/2 v/v yielded 200 mg of the title compound.

TLC: Rf=0.5, silica gel, heptane/ethyl acetate 1/2 v/v.

(d) HOOC—CH$_2$—D—Cha—Pro—Ppa—(2-oxazolyl)

To a solution of 0.20 g N—(t-butyloxycarbonylmethyl)(Boc)—D—Cha—Pro—Ppa(Teoc)-(2-oxazolyl) in 2 ml of dichloromethane was added 2 nd of trifluoroacetic acid and stirred at room temperature. After 4 hours the reaction mixture was concentrated and purified on a preparatieve HPLC Deltapack C18 15 μm 100 Å column using a gradient elution system of 20% A/80% B/0% C to 20% A/51% B/29% C over 45 min at a flow rate of 20 ml/min to give the title compound as two diastereomers.

Yield: 49 mg. Rt (LC): 27.83 min, 20% A/80% B to 20% A/20% B/60% C in 40 min.

Yield: 46 mg. Rt (LC): 30.04 min, 20% A/80% B to 20% A/20% B/60% C in 40 min.

EXAMPLE 45

HOOC—CH₂—D—Cha—Pro—Ppa—(2-thiazolyl)

(a) Boc—Ppa(Cbz)—OH

The pH of a solution of 70 g of H—Ppa—OH, 39.85 g of copper (II) sulphate pentahydrate and 147 g of benzyloxycarbonyloxysuccinimide was adjusted to 9 with 2N sodium hydroxide. The mixture was stirred for 16 hours at room temperature. The precipitate was collected and washed well with water. The filtercake was dissolved in dioxane and the pH adjusted to 12.5 with 4 N sodium hydroxide and 129 g of di—t-butyl dicarbonate were added. The mixture was stirred for 16 hours. The precipitate was collected and washed with dioxane. The filtrate was concentrated to a small volume and the pH was adjusted to 2.5. The residue was diluted with ethyl acetate. The organic layer was washed with water dried on sodium sulphate and evaporated to dryness to give 100 g of an oil.

TLC: Rf=0.77 in dichloromethane/methanol 9/1 v/v on silica gel.

(b) Boc—Ppa(Cbz)—N(Me)(OMe)

To a solution of 22.5g of Boc—Ppa(CBz)—OH in 500 ml of dichloromethane was added 7.54 g of N,O-dimethylhydroxylamine.HCl and 24.75 g of TBTU. The pH was adjusted at pH 8.5 with triethylamine. The mixture was stirred for 2 hours at room temperature, then washed with 1N hydrochloric acid, water, 5% sodium hydrogencarbonate solution and water, dried on sodium sulphate and evaporated in vacuo to yield 15.4 g as a white solid on crystallization from dfisopropyl ether.

TLC: Rf=0.5 in dichloromethanelethyl acetate 8/2 v/v on silica (c) Boc—Ppa(Cbz)-(2-thiazolyl)

To a cold (−78° C.), stirred solution of n-BuLi (0.11 mol) in diethyl ether (100 ml), was added, dropwise, a solution of 2-bromothiazole (18.2 g., 0.11 mol) in diethyl ether (100 ml). After the solution had been stirred at −78° C. for 30 min, a solution of Boc—Ppa(Cbz)—N(Me)(OMe) (15 g, 0.035 mol) in dry tetrahydrofiran (300 ml) was added slowly. The mixture was stirred at −78° C. for 1 hour, then 5% aqueous sodium hydrogencarbonate was added. The mixture was allowed to warm to room temperature and the layers were separated. The aqueous layer was extracted with ethyl acetate. The combined organic layers were washed with water, dried over sodium sulphate, filtered and evaporated yielding 15.1 g of an oil. The residue was purified by chromatography on silica (eluent: dichloromethane/methanol 99/1 v/v) to give 3.2 g of the title compound.

TLC: Rf=0.45, silica gel, dichloromethanetmethanol 95/5 v/v (d) H—Ppa(Cbz)-(2-thiazolyl).TFA N—Boc—Ppa(Cbz)-(2-thiazolyl) (500 mg) was dissolved in 10 ml trifluoroacetic acid/dichloromethane 1/1 v/v and stirred for 1 hour at room temperature. The crude amine was isolated as an oil in quantitative yield after removal of the solvent by evaporation, and used immediately to prepare N—(t-butyloxycarbonyimethyl)—N—Boc—D—Cha—Pro—Ppa(Cbz)-(2-thiazolyl).

TLC: Rf=0.40, silica gel, ethyl acelate/pyridinelacetic acid/water 63/20/6/11 v/v/v/v.

(e) N—(t-Butyloxycarbonylmethyl)—N—Boc—D—Cha—Pro—Ppa(Cbz)-(2-thiazolyl)

Isobutyl chloroformate (130 μl) was added to a stirred solution of N—(t-butyloxycarbonylmethyl)—N—Boc—D—Cha—Pro—OH (490 mg) and N,N-diisopropylethylamine (170 μl) in dry N,N-dimethylformamide (12 ml) at −15° C. under nitrogen atmosphere. After 15 min H—Ppa(Cbz)-(2-thiazolyl).TFA dissolved in dry N,N-dimethylformamide (10 ml), was added dropwise to the cold mixed anhydride solution, maintaining the pH at 8.5 by addition of N,N-diisopropylethylamine. The reaction mixture was stirred for 60 min at −15° C. The reaction mixture was evaporated to dryness. The residue was dissolved in ethyl acetate and successively washed with 2% aqueous citric acid-solution, water and brine, dried over sodium sulphate and concentrated in vacuo. The residue was purified by chromatography on silica (eluent: dichloromethane/methanol 99/1 v/v to yield 470 mg of N—(tert-butyloxycarbonylmethyl)—N—Boc—D—Cha—Pro—Ppa(Cbz)-(2-thiazolyl).

TLC: Rf=0.65, silica gel, dichloromethanelmethanol 95/5 v/v.

(f) HOOC—CH₂—D—Cha—Pro—Ppa—(2-thiazolyl)

A solution of 470 mg of N—(t-butyloxycarbonylmethyl)—N—Boc—D—Cha—Pro—Ppa (Cbz)-(2-thiazolyl) in 5 ml trifluoroacetic acid and 0.5 ml thioanisole was stirred for 4 hours at room temperature. The solvent was removed in vacuo and the residue was purified on preparative HPLC Delta-Pak CARRP column using a gradient elution system of A: 20%; B: 70%; C: 10% to A: 20%; B: 20%; C: 60% over 40 nin at a flowrate of 80 ml/min.

(A: 0.5 M phosphate buffer pH=2.1; B: water; C: acetonitrile:water 3:2 v/v).

Yield 177 mg. $R_t$ (LC): 33.57 min. 20% A/80% B to 20% A/20% B/60% C in 40 min.

EXAMPLE 46

HOOC—CH₂—p—MeO—D—Phe—Pro—Ppa—(2-thiazolyl)

The synthesis of N—(t-butyloxycarbonylmethyl)—N—Boc—p—MeO—D—Phe—Pro—OH has been described in example 6. The coupling to H—Ppa(Cbz)-(2-thiazolyl) (135 mg), subsequent deprotection and purification were done according to the procedure descnbed in example 45 resulting in two separated diastereomers.

Yield: 37 mg. $R_t$: 27.17 min., 20% A, 80% B, 0% C to 20% A, 20% B, 60% C in 40 min.

Yield: 47 mg. $R_t$: 30.15 min., 20% A, 80% B, 0% C to 20% A, 20% B, 60% C in 40 min.

EXAMPLE 47

HOOC—CH₂—p—Cl—D—Phe—Pro—Ppa—(2-thiazolyl)

The synthesis of N—(t-butyloxycarbonylmethyl)—N—Boc—p—Cl—D—Phe—Pro—OH has been described in example 5. The coupling to H—Ppa(Cbz)-(2-thiazolyl) (322 mg), subsequent deprotecfion and purification were done according to the procedure described in example 45 resulting in two separated diastereomers.

Yield: 73 mg. $R_t$: 31.07 min., 20% A, 60% B, 20% C to 20% A, 0% B, 80% C in 30 min.

Yield: 94 mg. $R_t$: 18.21 min., 20% A, 60% B, 20% C to 20% A, 0% B, 80% C in 30 min.

EXAMPLE 48

HOOC—CH₂—D—Nle—Pro—Ppa—(2-thiazolyl)

The synthesis of N—(t-butyloxycarbonylmethyl)—N—Boc—D—Nle—Pro—OH has been described in example 8.

(a) Boc—Ppa—N(Me)OMe

To a solution of Boc—Ppa(Cbz)—N(Me)OMe (example 45b) (820 mg) in N,N-dimethylformamide (25 ml) was added 2N hydrochloric acid (0.915 ml) and 10% Paladium on carbon (100 mg) whereafter the mixture was hydrogenated during 1 hour at room tempemture. The reaction mixture was filtered over diacel, washed with N,N- dimethylformamide and neutralised with triethylamine (0.15 ml). The product was used crude in the synthesis of Boc—Ppa(Teoc)—N(Me)OMe.

(b) Boc—Ppa(Teoc)—N(Me)OMe

To the crude solution of Boc—Ppa—N(Me)OMe were successively added 1-[2-(trimethylsilyl)ethoxycarbonyloxy]pyrrolidin-2,5-dione (TeocOSu, reference: Synthesis 1987, 346) (567 mg) and triethylanine (0.350 ml) and stirred for 4.5 hours at room temperature under a nitrogen atmosphere. The pH of the solution was kept at 8 with triethylamine. The solvent was removed by evaporation at reduced pressure, dichoromethane was added and the solution was washed with 0.1N hydrochloric acid (100 ml), water, 5% sodium hydrogen-carbonate solution and water, dried over magnesium sulphate and concentrated in vacuo. The residue was purified by chromatography on silica gel eluting with heptane/ethyl acetate 8/2 v/v as eluent. Yield: 784 mg.

TLC: Rf=0.37, silica gel, heptane/ethyl acetate 1/1 v/v.

(c) Boc—Ppa(Teoc)-(2-thiazolyl)

To a cold (−70° C.) solution of n-butyllithium in diethyl ether (68.4 ml 1.07 mol/l), under a nitrogen atmosphere, was slowly added a solution of 2-bromothiazole (6.59 ml) in diethyl ether (50 ml) and stirred for 30 min. at −70° C. This lithiumthiazolide solution was added very slowly to a cold (−70° C.) solution of Boc—Ppa(Teoc)—N(Me)OMe (16.8 g) in dry tetrahydrofuiran (150 ml) and stirred for 1 hour at −70° C. under a nitrogen atmosphere. The reaction mixture was diluted with 0.2 N hydrochloric acid (200 ml), extracted three times with dichloromethane, the organic layers were washed with water, 5% sodium bydrogencarbonate solution and water, dried over magnesium sulphate and concentrated in vacuo. The residue was chromatographed on silica gel eluting with heptanelethyl acetate 8/2 v/v as eluent. Yield: 11.35 g.

TLC: Rf=0.68 , silica gel, heptane/ethyl acetate 1:1 v/v.

(d) H—Ppa(Teoc)-(2-thiazolyl).TsOH

To a solution of Boc—Ppa(Teoc)-(2-thiazolyl) (2.5 g) in diethyl ether (100 ml) was added p-toluenesulfonic acid (1.2 g). The reaction mixture was slowly evaporated at 30° C. at 200 mbar for 1.5 hour at 15 mbar. Yield: 3.03 g.

(e) HOOC—CH$_2$—D—Nle—Pro—Ppa—(2-thiazolyl)

The coupling of N—(t-butyloxycarbonylmethl)—N—Boc—D—Nle—Pro—OH to H—Ppa(Teoc)-(2-thiazolyl) .TsOH (307 mg), su uent deprotection and purification were done according to example 45 resulting in two separated diastereomers.

Yield: 96 mg. R$_t$: 23.45 min., 20% A, 80% B, 0% C to 20% A, 20% B, 60% C in 40 min.

Yield: 99.6 mg. R$_t$: 26.60 min., 20% A, 80% B, 0% C to 20% A, 20% B, 60% C in 40 min.

EXAMPLE 49
HOOC—CH$_2$—m—Cl—D,L—Phe—Pro—Ppa—(2-thiazolyl)

The synthesis of N—(t-butyloxycarbonylmethyl)—N—Boc—m—Cl—D,L—Phe—Pro—OH has been described in example 4. The coupling to H—Ppa(Teoc)-(2-thiazolyl) .TsOH (325 mg), the subsequent deprotection and the purification were done according to the procedure described in example 48 resulting in four separated diastereomers.

Yield: 80 mg. R$_t$: 28.68 min., 20% A, 80% B, 0% C to 20% A, 20% B, 60% C in 40 min.

Yield: 40 mg. R$_t$: 31.02 min., 20% A, 80% B, 0% C to 20% A, 20% B, 60% C in 40 min.

Yield: 72 mg. R$_t$: 32.62 min., 20% A, 80% B, 0% C to 20% A, 20% B, 60% C in 40 min.

Yield: 52 mg. R$_t$: 34.22 min., 20% A, 80% B, 0% C to 20% A, 20% B, 60% C in 40 min.

EXAMPLE 50
HOOC—CH$_2$—D—Dpa—Pro—Ppa—(2-thiazolyl)

(a) Boc—D—Dpa—Pro—OBzl

Boc—D—Dpa—Pro—OBzl was obtained by reacting Boc—D—Dpa—OH (4.77 g) with H—Pro—OBzl (3.8 g) according to the coupling conditions described in example 1. Yield: 8.4 g.

TLC: Rf=0.95, silica gel, ethyl acetate/pyridine/acetic acid/water 560/31/18/7 v/v/v/v.

(b) Boc—D—Dpa—Pro—OH

Boc—D—Dpa—Pro—OH was obtained by catalytic hydrogenation of Boc—D—Dpa—Pro—OBzl (7 g) according to the procedure descnbed in example 1. Yield: 5.5 g.

TLC: Rf=0.59, silica gel, ethyl acetatelpyridine/acetic acid/water 520/31/18/7 v/v/v/v.

(c) Boc—D—Dpa—Pro—Ppa(Teoc)-(2-thiazolyl)

The coupling of Boc—D—Dpa—Pro—OH (500 mg) to H—Ppa(Teoc)-(2-thiazolyl).TsOH (573 mg) was done according to the procedure described in example 48. Yield: 712 mg.

TLC: Rf=0.44, silica gel, heptane/ethyl acetate 4:6 v/v.

(d) N—(t-Butyloxycarbonylmethyl)—D—Dpa—Pro—Ppa(Teoc)-(2-thiazolyl)

Boc—D—Dpa—Pro—Ppa(Teoc)-(2-thiazolyl) (712 mg) was treated with p-toluene suifonic acid according to the procedure described in example 48 to yield H—D—Dpa—Pro—Ppa(Teoc)-(2-thiazolyl) (761 mg). N—(t-butyioxycarbonylmethyl)—D—Dpa—Pro—Ppa(Teoc)-(2-thiazolyl) was obtained from the alkylation of H—D—Dpa—Pro—Ppa(Teoc)-(2-thiazolyl) (761 mg) with t-butyl bromoacetate (0.138 ml) according to the procedure described in example 1. Yield: 674 mg.

TLC: Rf=0.54, silica gel, heptane/ethyl acetate 3/7 v/v.

(e) HOOC—CH$_2$—D—Dpa—Pro—Ppa—(2-thiazolyl)

The subsequent deprotection and the purification were done according to the procedure described in example 48 resulting in two separated diastereomers.

Yidd: 64 mg. R$_t$: 35.16 min., 20% A, 80% B, 0% C to 20% A, 20% B, 60% C in 40 min.

Yield: 96 mg. R$_t$: 36.80 min., 20% A, 80% B, 0% C to 20% A, 20% B, 60% C in 40 min.

EXAMPLE 51
HOOC—CH$_2$—D—Cha—Ohi—Ppa—(2-thiazolyl)

(a) N—(t-Buiyoxicarbonylmethl)—N—Boc—D—Cha—OH

N—(t-Butyloxycarbonylmethyl)—N—Boc—D—Cha—OH was prepared as described in example 45.

(b) H—Ohi—OMe.HCl

To a −15° C. solution of dry methanol (10 ml), 0.43 ml (0.7 g) of thionylchloride was added dropwise. The mixture was stirred for 20 min at −10° C. after which octahydro indolin-2-carboxylic acid (H—Ohi—OH) (0.5 g) was added and the solution was refluxed for 3 hours. The mixture was concentrated and coevaporated with methanol in vacuo to yield 665 mg H—Ohi—OMe.HCl.

TLC: Rf=0.68, silica gel, butanoupyridine/acetic acid/water 4/1/1/2 v/v/v/v.

(c) N—(t-Butyloxycarbonylmethyl)—N—Boc—D—Cha—Ohi—OMe

To a cold (0° C.) solution of N—(t-butyloxycarbonylmethyl)—N—Boc—D—Cha—OH (1.2 g) in dichloromethane (40 ml) were added 1-hydroxy benzotriazole (460 mg), dicyclohexyl carbodiimide (700 mg) and stirred for 20 min at 0° C. Next H—Ohi—OMe.HCl (665 mg) and N,N-diisopropylethylamine (0.075 ml) were added to this reaction mixture. The mixture was stiffed at 0° C. for 1 h. and then kept at room temperature during 7 days keeping the pH of the solution at 7 with N,N-diisopropylethylamine. The mixture was cooled to −20° C. and dicyclohexylurea was removed by filtration. The filtrate was evaporated to dryness. The residue was dissolved in ethyl acetate and washed with 1N hydrochloric acid, saturated sodium hydrogencarbonate and brine, dried over sodium sulphate and concentrated in vacuo. The residue was chromatographed on silica gel eluting with heptane/ethyl acetate 3/1 v/v as eluent.

Yield: 1.07 g.

TLC: Rf=0.41, silica gel, heptane/ethyl acetate 3/1 v/v.

(d) N—-(t-Butyloxycarbonylmethyl)—N—Boc—D—Cha—Ohi—OH

To a solution of N—(t-butyloxycarbonylmethyl)—N—Boc—D—Cha—Ohi—OMe (1.05 g) in dioxane/water 211 v/v (30 ml) lithium hydroxide monohydrate(0.32 g) was added. The mixture was stirred at room temperature for 6.5 hours. Dioxane was removed by evaporation at reduced pressure, ethyl acetate was added, the pH was adjusted to 1.5 using hydrochloric acid and the water layer was extracted three tines with ethyl acetate. The organic layer was washed with water and brine, dried on sodium sulphate and concentrated in vacuo. The residue was chromatographed on silica gel eluting with heptane/ethyl acetate 1/2 v/v as eluent. The fractions containing N—(t-butyloxycarbonylmethyl)—N—Boc—D—Cha—Ohi—OH were pooled and evaporated.

Yield: 500 mg.

TLC: Rf=0.25, silica gel, ethyl acetate/heptane 2/1 v/v.

(e) HOOC—CH$_2$—D—Cha—Ohi—Ppa—(2-thiazolyl)

The coupling of N—(t-butyloxycarbonylmethyl)—N—Boc—D—Cha—Ohi—OH and H—Ppa(Teoc)-(2-thiazolyl) .TsOH (428 mg), subsequent deprotection and the purification were done according to the procedure described in example 48 resulting in two separated diastereomers.

Yield: 85 mg. R$_t$: 37.72 min., 20% A, 80% B, 0% C to 20% A, 20% B, 60% C in 40 min.

Yield: 127 mg. R$_t$: 42.46 min., 20% A, 80% B, 0% C to 20% A, 20% B, 60% C in 40 min.

EXAMPLE 52

HOOC—CH$_2$—D—Cha—Pro(4-cis-ethyl)—Ppa—(2-thiazolyl)

(a) N—(t-Butyloxycarbonylmethyl)—N—Boc—D—Cha—Pro(4cis-ethyl)—OEt

N—(t-Butyloxycarbonylmethyl)—N—Boc—D—Cha—OH was prepared as described in example 45. To a cold (0° C.) solution of N—(t-butyloxycarbonylmethyl)—N—Boc—D—Cha—OH (3.7 g) in dichloromethane (15 ml) were added 1-hydroxy benzotriazole (1.43 g), dicyclohexyl carbodiimide (2.18 g) and stirred for 15 min at 0° C. Next H—Pro(4-cis-ethyl)—OEt.HCl (1.99 g), which was prepared according to WO 95123608, and N,N-diisopropylethylamine (0.150 ml) were added to this reaction mixture. The mixture was stirred at 0° C. for 1 hour and then kept at room temperature during 2 hours keeping the pH of the solution at 7 with N,N-diisopropylethylamine. The mixture was cooled to −20° C. and dicyclohexylurea was removed by filtration. The filtrate was evaporated to dryness. The residue was dissolved in ethyl acetate and washed with 1 N hydrochloric acid, saturated sodium hydrogencarbonate, water and brine, dried over sodium sulphate and concentrated in vacuo The residue was chromatographed on silica gel eluting with heptane/ethyl acetate 3/1 v/v as eluent. The fractions containing N—(t-butyloxycarbonylmethyl)—N—Boc—D—Cha—Pro(4cis-ethyl)—OEt were pooled and evaporated.

Yield: 3.87 g.

TLC: Rf=0.46, silica gel, heptanelethyl acetate 3/1 v/v.

(b) N—(t-butyioxycarbonylmethyl)—N—Boc—D—Cha—Pro(4-cis-ethyl)—OH

To a solution of N—(t-butyloxy-carbonylmethyl)—N—Boc—D—Cha—Pro(4cis-ethyl)—OEt (3.85 g) in dioxane/water 9/1 v/v (50 al) 1N sodium hydroxide (7.5 ml) was added. The mixture was stirred at room temperature. After 60 hours 70 mg lithium hydroxide monohydrate in 10 ml of water was added and stirred for an additional 12 hours. The reaction mixture was diluted with 100 ml of water, the pH was adjusted to 1.5 with hydrochloric acid and the water layer was extracted three times with dichloromethane. The organic layer was washed with water and brine, dfied on sodium sulphate and concentrated in vacuo. The residue was chromatographed on silica gel eluting with heptanelethyl acetate 1/2 v/v as eluent. The fractions containing N—(t-butyloxycabonylmethyl)—N—Boc—D—Cha—Pro(4-cis-ethyl)—OH were pooled and evaporated.

Yield: 1.39 g.

TLC: Rf=0.79, silica gel, ethyl acetate/pyridinelacetic acidlwater 126/20/11/6 v/v/v/v.

(c) HOOC—CH$_2$—D—Cha—Pro(4-cis-ethyl)—Ppa—(2-thiazolyl)

The coupling of N—(t-butyloxycarbonylmethyl)—N—Boc—D—Cha—Pro(4-cis-ethyl)—OH and H—Ppa(Teoc)-(2-thiazolyl).TsOH (325 mg), subsequent deprotection and purification were done according to the procedure described in example 48 resulting in two separated diastereomers.

Yield: 77.5 mg. R$_t$: 36.61 min.,20% A, 80% B, 0% C to 20% A, 20% B, 60% C in 40 min.

Yield: 104 mg. R$_t$: 40.05 min., 20% A, 80% B, 0% C to 20% A, 20% B, 60% C in 40 min.

EXAMPLE 53

HOOC—CH$_2$—D—Coa—Pro—Ppa—(2-thiazolyl)

(a) Diethyl 2-acetylamino-2-(cyclooctylmethyl)-malonate

To a cold (0° C.) suspension of sodium hydride (5.36 g) in dioxane (100 ml) was added dropwise (very slow) dry ethanol (134 ml) and stirred for 1.5 hours at 0° C. under a nitrogen atmosphere. This resulting sodium ethanolate solution was added dropwise to a solution of cyclooctylmethylbrornide (example 7(a)) (27.49 g), sodium iodide (2.0 g) and diethyl acetylaminomalonate (29.10 g) in dioxane (200 ml)/ethanol (20 ml) and stirred vigorously for 165 hours at 80° C. The solvent was removed by evaporation at reduced pressure, ethyl acetate was added, washed with water, 5% sodium hydrogencrbonate solution and brine, dried on magnesium sulphate and concentrated in vacuo. The residue was chromatographed on silica gel eluting with heptanelethyl acetate 7/3 v/v as luent. The fiwtons containing the desired compound were pooled and evaporated.

Yield: 19.60 g. TLC: Rf=0.53, silica gel, hepta/ethyl acetate 7/3 v/v.

(b) H—D,L—Coa—OH

The amino acid H—Coa—OH was obtained by reflwung a solution of diethyl 2-acetylamino-2-(cyclooctylmethyl) malonate (19.60 g) in 4N hydrochloric acid/acetic acid 2:1 v/v (450 ml) for 75 hours After cooling, the crystals were collected by filtration and washed with diethyl ether.

Yield: 9.83 g.

TLC: Rf=0.59, silica gel, ethyl acetate/pyridinelacetic acid/water 63/20/6/11 v/v/v/v.

(c) N—(t-Butyloxycarbonylmethyl)—N—Boc—D,L—Coa—Pro—OBzl

The synthesis of N—(t-butyloxycarbonylmethyl)—N—Boc—Coa—Pro—OBzl was performed according to the procedures described in example 1.

(d) HOOC—CH$_2$—D—Coa—Pro—Ppa—(2-thiazolyl)

The N—(t-butyloxycarbonylmetbyl)—N—Boc—Coa—Pro—OH was obtained by hydrogenation of N—(t- butyloxycarbonylmethyl)—N—Boc—Coa—Pro—OBzl (19.61 g) according to the procedure described in example 1. The resulting oil was treated with diethyl ether after which both diastereomers of N—(t-butyloxycarbonylmethyl)—N—Boc—Coa—Pro—OH were separated by filtration. The filtrate was evaporated at reduced pressure (yield 9.34 g.) and used for coupling to H—Ppa(Teoc)-(2-thiazolyl).TsOH (400 mg), the subsequent deprotection and the purification were done according to the procedure described in example 48 resulting in two separated diastereomers.

Yield: 137 mg. $R_t$: 36.10 min., 20% A, 80% B, 0% C to 20% A, 20% B, 60% C in 40 min.

Yield: 139 mg. $R_t$: 38.94 min., 20% A, 80% B, 0% C to 20% A, 20% B, 60% C in 40 min.

EXAMPLE 54

HOOC—CH$_2$—D—Cha—Azt—Ppa—(2-thiazolyl)

(a) N—(t-Butyloxycarbonylmethyl)—N—Boc—D—Cha—OH

N—(t-Butyloxycarbonylmethyl)—N—Boc—D—Cha—OH was prepared as described in example 1.

(b) N—(t-Butyloxycarbonylmethyl)—N—Boc—D—Cha—Azt—OH

Isobutyl chlorofornate (0.71 ml) was added dropwise to a cooled (-15--20° C.) solution of N—(t-butyloxycarbonylmethyl)—N—Boc—D—Cha—OH (1.90 g) and N-methyl morpholine (0.6 ml) in 15 ml dichloromethane. After 45 min, H—Azt—OH (0.50 g) was added. After 1 hour, the organic phase was extracted with water, the organic layer was dried on sodium sulphate, filtered and the solvent was removed under pressure. Yield: 2.3 g of the title compound as a nearly colorless oil.

FAB—MS: m/e=469 (M+H$^+$).

(c) HOOC—CH$_2$—D—Cha—Azt—Ppa—(2-thiazolyl)

The coupling to H—Ppa(Teoc)-(2-thiazolyl) (428 mg), the subsequent deprotection and the purification were done according to the procedure described in example 48 resulting in two separated diastereomers.

Yield: 72 mg. $R_t$: 28.10 min., 20% A, 80% B, 0% C to 20% A, 20% B, 60% C in 40 min.

Yield: 88 mg. $R_t$: 31.46 min., 20% A, 80% B, 0% C to 20% A, 20% B, 60% C in 40 min.

EXAMPLE 55

HOOC—(CH$_2$)$_2$—D—Cha—Pro—Ppa—(2-thiazolyl)

(a) N—(t-Butyloxycarbonyl)ethyl)—D—Cha—OMe

To a suspension of 7.11 g of D—Cha—OMe.HCl in 25 ml of acetonitrile was added 2.6 ml of N,N-diisopropylethylamine and 25 ml of tert-butyl aciylate. This reaction mixture was heated at 40° C. and mantained at pH 8 (spot test on a moist pH paper) using N,N-diisopropylethyiamine. After one week the reaction mixture was concentrated. The residue was dissolved in ethyl acetate, washed with water and brine, dried (sodium sulphate) and concentrated to afford 11.78 g of the title compound that was used without further purification.

TLC: Rf=0.7, silica gel, ethyl acetatefheptane 1/1 v/v.

(b) N-(2-(t-Butyloxycarbonyl)ethyl—N—Boc—D—Cha—OMe

According to the procedure described for N—(t-butyloxycarbonylmethyl)—N—Boc—D—Cha—OMe (example 1) N-(2-(t-butyloxycanylethyl)—D—Cha—OMe (11.78 g) was transformed into N-(2-(t-butyloxyearbonyl)ethyl)—N—Boc—D—Cha—OMe (8.78 g).

TLC: Rf=0.7, silica gel, ethyl acetateheptane 1/2 v/v.

(c) N-(2-(t-Butyloxycarbonyl)ethyl)—N—Boc—D—Cha—OH

According to the procedure descrbed for N—(t-butyloxycarbonylmethyl)—N—Boc—D—Cha—OH (example 1) N-(2-(t-butyloxycarbonyl)ethyl)—N—Boc—D—Cha—OMe (10.0 g) was saponified to give N-(2-(t-butyloxycarbonyl)ethyl)—N—Boc—D—Cha—OH (4.31 g).

TLC: Rf=0.1, silica gel, ethyl acetate/heptane 1/5 v/v.

(d) N-(2-(t-Butyloxycarbonyl)ethyl)—N—Boc—D—Cha—Pro—OBzl

According to the procedure described for N—(t-butyloxycarbonylmethyl)—N—Boc—D—Cha—Pro—OBzl (example 1) N-(2-(t-butyloxycarbonyl)ethyl)—N—Boc—D—Cha—OH (3.14 g) was coupled with Pro—OBzl.HCl to give N-(2-(t-butyloxycarbonyl)ethyl)—N—Boc—D—Cha—Pro—OBzl (4.36 g).

TLC: Rf=0.5, silica gel, ethyl acetate/heptane 1/2 v/v.

(e) N-(2-(t-Butyloxycarbonyl)ethyl)—N—Boc—D—Cha—Pro—OH

According to the procedure described for N—(t-butyloxycarbonylmethyl)—N—Boc—D—Cha—Pro—OH (example 1) N-(2-(t-butyloxycarbonyl)ethyl)—N—Boc—D—Cha—Pro—OBzl (4.33 g) was hydrogenated to give N-(2-(t-butyloxycarbonyl)ethyl)—N—Boc—D—Cha—Pro—OH (3.96 g).

TLC: Rf=0.15, silica gel, ethyl acetate.

(f) N-(2-(t-Butyloxycarbonyl)ethyl)—N—Boc—D—Cha—pro—Ppa(Teoc)-(2-thiazolyl)

According to the procedure described for N—(t-butyloxycarbonytznethyl)—N—Boc—D—Cha—Pro—Ppa(Teoc)-(2oxazolyl) (example 44) N-(2-(t-butyloxycarbonyl)ethyl)—N—Boc—D—Cha—Pro—OH (342 mg) was coupled with H—Ppa(Teoc)-(2-thiazolyl).TsOH (described in example 48) to give N-(2-(t-butyloxycarbonyl)ethyl)—N—Boc—D—Cha—Pro—Ppa(Teoc)-(2-thiazolyl) (468 mg).

TLC: Rf=0.25, silica gel, ethyl acetate/heptane 1/1 v/v.

(g) HOOC—CH$_2$CH$_2$—D—Cha—Pro—Ppa—(2-thiazolyl)

According to the procedure described for HOOC—CH$_2$—D—Cha—Pro—Ppa—(2-oxazolyl) (example 44) N-(2-(t-Butyloxycarbonyl)ethyl)—N—Boc—D—Cha—Pro—Ppa(Teoc)-(2-thiazolyl) (468 mg) was deprotected to give N—(HOOC—CH$_2$CH$_2$)—D—Cha—Pro—Ppa—(2-thiazolyl) as two diastereomers.

Yield: 123 mg. $R_t$ (LC): 30.2 min, 20% A, 80% B to 20% A, 20% B, 60% C in 40 min.

Yield: 138 mg. $R_t$ (LC): 33.6 min, 20% A, 80% B to 20% A, 20% B, 60% C in 40 min.

EXAMPLE 56

HOOC—CH$_2$—(N—Me)—D—Cha—Pro—Ppa—(2-thiazolyl)

Boc—D—Cha—OH (20 g) was dissolved in dichloromethane/methanol 9/1 v/v (400 ml). 2-(1H-benzotriazol-1-yl)-1,1,3,3-tetramethyluronium tetrafluoroborate (22.7 g) was added and the solution adjusted to pH 8 by addition of triethylamine (10 ml). The reaction mixture was stirred for 16 hours at room temperature. The mixture was washed successively with cold 1 N hydrochloric acid solution, water, 5% sodium hydrogencarbonate, and water and dried over sodium sulphate. The filtrate was evaporated and the residue was chromatographed on silica gel eluting with ethyl acetate/heptane 2,3 v/v as eluent. The fractions containing Boc—D—Cha—OMe were pooled and evapoorated Yield: 19.38 g.

TLC: Rf=0.90, silica gel, ethyl acetate/heptane 3/1 v/v.

(b) Boc—(N—Me)—D—Cha—OMe

Boc—D—Cha—OMe (19.35 g) was dissolved in 200 ml dry N,N-dimethylformamide under nitrogen atnosphere. Methyliodide (4.22 ml) was added and the mixture was cooled to 0° C. 2.71 g of sodium hydride (60% dispersion in oil) was added and the reaction mixture was stirred for 3 hours at room temperature. The micure was partially concentrated, ethyl acetate was added and the organic layer was washed with 0.1 M hydrochloric acid, water, 5% sodium hydrogencarbonate solution and brine, dried over sodium sulphate and concentrated. Yield 21.07 g.

TLC: Rf=0.55, silica gel, ethyl acetate/heptane 3/7 v/v.

(c) Boc—(N—Me)—D—Cha—OH

A solution of Boc—(N—Me)—D—Cha—OMe (20 g) in 400 ml of dioxane/water 9/1 v/v was treated with sufficient 2 M sodium hydroxide solution to keep the pH at 12 for 16 hours at room temperature. After acidification, the mixture was poured into water and was extracted with dichloromethane. The organic layer was washed with water and was dried over sodium sulphate. The filtrate was evaporated and yielded 21.2 g of Boc—(N—Me)—D—Cha—OH.

TLC: Rf=0.75, silica gel, ethyl acetate/pyridine/acetic acid/water 63/20/6/11 v/v/v/v.

(d) Boc—(N—Me)—D—Cha—OBzl

Boc—(N—Me)—D—Cha—OH (2 g) was dissolved in dichloromethane (20 ml). Benzylalcohol (0.76 g) and 2-(1H-benzotriazol-1-yl)-1,1,3,3-tetramethyluronium tetrafluoroborate (2.24 g) were added and the solution adjusted to pH 8 by addition of triethylamine (10 ml). The reaction mixture was stirred for 1 hour at room temperature. The mixture was washed successively with cold 1 N hydrochloric acid solution, water, 5% sodium hydrogencarbonate, and water and dried over sodium sulphate. The filtrate was evaporated and the residue was chromatographed on silica gel eluting with ethyl acetate/heptane 1/3 v/v as eluent. The fiactions containing (N—Me)—Boc—D—Cha—OBzl were pooled and evaporated. Yield: 1.56 g.

TLC: Rf=0.75, silica gel, ethyl acetate/heptane 3/1 v/v.

(e) H—(N—Me)—D—Cha—OBzl

Boc—(N—Me)—D—Cha—OBzl (1.56 g) was treated with 50% trifluoroacetic acididichloromethane (20 ml) for 1 hour at room temperature. The reaction mixture was evaporated to dryness yielding 1.6 g of the title compound.

TLC: Rf=0.50, silica gel, ethyl acetate/pyridine/acetic acid/water 63/20/6/11 v/v/v/v.

(f) N—(t-Butyloxycarbonylmethyl)-(N—Me)—D—Cha—OBzl t-Butyl bromoacetate (0.81 g) was added to a stirred solution of H—(N—Me)—D—Cha—OBzl (1.6 g) in 40 ml of acetonitrile. Tetrabutyl ammoniumiodide (150 mg) was added and the pH of the mixture was adjusted to 8.5 with N,N-diisopropylethylamine. The mixture was stirred for 16 hours at 50° C. and evaporated in vacuo. The residue was dissolved in ethyl acetate and the solution was washed with 5% sodium hydrogencarbonate solution and water, dried on sodium sulphate and evaporated in vacuo. Chromatography over silica gel eluting with heptane/ethyl acetate 4/1 v/v gave 1.11 g of N—(t-butyloxycarbonylmethyl)-(N—Me)—D—Cha—OBzl.

TLC: Rf=0.95, silica gel, ethyl acetate/pyridine/acetic acid/water 63/20/6/11 v/v/v/v.

(g) N—(t-Butyloxycarbonylmethyl)-(N—Me)—D—Cha—OH

10% Palladium on charcoal (100 mg) and 1.43 ml of a 2 M hydrochloric acid were added to a solution of N—(t-butyloxycarbonylmethyl)-(N—Me)—D—Cha—OBzl (1.11 g) in methanol (20 ml). The reaction mixture was hydrogenated at atmospheric pressure at room temperature for 1 hour. The palladium catalyst was removed by filtration and the solvent removed by evaporation at reduced pressure yielding 970 mg of N—(t-butyloxycarbonylmethyl)-(N—Me)—D—Cha—OH.

TLC: Rf=0.75, silica gel, ethyl acetate/pyridine/acetic acid/water 163/20/6/11 v/v/v/v.

(h) HOOC—CH$_2$—(N—Me)—D—Cha—Pro—Ppa—(2-thiazolyl) N—(t-Butyloxycarbonylmethyl)-(N—Me)—D'Cha—Pro—OH was prepared according to the procedure as described for example 1. The mixed anhydride-couplin& the deprotection and the purification were done according to example 48. Yield two diastereomers both 79 mg.

A: R$_t$ (LC): 30.87 min; 20% A/80% B to 20% A/20% B/60% C in 40 min

B: R$_t$ (LC): 34.58 min; 20% A/80% B to 20% A/20% B/60% C in 40 min

EXAMPLE 57

EtOOC—CH$_2$—D—Cha—Pro—Ppa—(2-thiazolyl)

N—(t-Butyloxycarbonylmethyl)—N—Boc—D—Cha—Pro—Ppa(Teoc)-(2-thiazolyl) was prepared according to the procedure described in example 48. Deprotection was carried out with 3M hydrogen chloridclethanol. Purification yielded two diastereomers: 37 mg and 44 mg.

A: R$_t$ (LC): 35.24 min. 20% A/80% B to 20% A/20% B/60% C in 40 min.

B: R$_t$ (LC): 38.12 min. 20% A/80% B to 20% A/20% B/60% C in 40 min.

EXAMPLE 58

H—(N—Me)—D—Cha—Pro—Ppa—(2-thiazolyl)

Boc—(N—Me)—D—Cha—Pro—OH

The synthesis of Boc—(N—Me)—D—Cha—Pro—OH is described in example 16.

N—Me—D—Cha—Pro—Ppa—(2-thiazolyl)

According to the methods as described in example 45, Boc—(N—Me)—D—Cha—Pro—OH (400 mg) was coupled with H—Ppa(Cbz)-(2-thiazolyl).TFA. The obtained tripeptide was treated in a mixture of TFA and thioanisole (see example 45) and purified by HPLC to afford the title compound (218 mg) as a mixture of diastereomers.

R$_t$ (LC): 31.96 min, 20% A, 80% B to 20% A, 20% B and 60% C in 40 min.

EXAMPLE 59

EthylSO$_2$—D—Cha—Pro—Ppa—(2-thiazolyl)

(a) EthylSO$_2$—D—Cha—Pro—OH

The synthesis of ethylSO$_2$—D—Cha—Pro—OH is described in example 18.

(b) EthylSO$_2$—D—Cha—Pro—Ppa—(2-thiazolyl)

Coupling of ethylSO$_2$—D—Cha—Pro—OH (300 mg) with H—Ppa(Cbz)-(2-thiazolyl) as in example 45, afforded ethylSO$_2$—D—Cha—Pro—Ppa(Cbz)-(2-thiazolyl) (560 mg) after purification. Deprotection and purification according to the methods in example 45 gave ethylSO$_2$—D—Cha—Pro—Ppa—(2-thiazolyl) (190 mg) as a diastereomeric mixture.

R$_t$ (LC): 26.67 and 28.20 min, 20% A, 60% B and 20% C to 100% C in 40 min.

EXAMPLE 60

EthylSO$_2$—D—Phe—Pro—Ppa—(2-thiazolyl)

Coupling of ethylSO$_2$—D—Phe—Pro—OH (example 26) with H—Ppa(Teoc)-(2-thiazolyl).TsOH (example 47), according to the procedures as descibed in example 48, afforded the filly protected tripeptide. After deprotection (see example 48), two diastereomers could be seperated by HPLC.Yield of the two diastereomers:

80 mg. R$_t$ (LC): 39.87 min, 20% A, 80% B to 20% A, 20% B and 60% C in 40 min.

69 mg. R$_t$ (LC): 42.45 min, 20% A, 80% B to 20% A, 20% B and 60% C in 40 min.

EXAMPLE 61
BenzylSO$_2$—norLeu(cyclo)—Gly—Ppa—(2-thiazolyl)

235 mg BenzylSO$_2$—norLeu(cyclo)—Gly—OH (see example 12) was coupled with H—Ppa(Cbz)-(2-thiazolyl).TFA under the same conditions as described in example 45. Removal of the protecting group from the obtained tripeptide (example 45) gave, after HPLC purification, the two separate diastereomers:

Yield: 99 mg. R$_t$ (LC): 37.99 min, 20% A, 80% B to 20% A, 20% B and 60% C in 40 min.

Yield: 86 mg. R$_t$ (LC): 38.68 min, 20% A, 80% B to 20% A, 20% B and 60% C in 40 min.

EXAMPLE 62
Solid-phase synthesis of compounds of fonnula HOOC—CH$_2$—D—Cha—X—Ppa—(2-thiazolyl) (Table 62)

(a) Teoc—Ppa(Boc)—OH

To a solution of 18.4 g of H—Ppa—OH and 6.8 g of copper (II) sulfate pentahydrate in water (312 ml) and dioxane (234 ml) was added 33.9 g of di—t-butyl dicarbonate while the pH was adjusted to 9 with 4 N sodium hydroxide. The mixture was stirred for 16 hours at room temperature. The precipitate was collected and washed with water. The filter cake was suspended in dioxane and the pH adjusted to 12.5 with 4N sodium hydroxide. 24 ml of 2-trimethylsilylethyloxycarbonyl chloride was added in two portions with 0.5 hour interval. The mixture was stirred for 16 hours The precipitate was filtered and washed with dioxane. The filtrate was concentrated to a small volume and the pH was adjusted to 2.5. The mixture was diluted with ethyl acetate, washed with water, dried on sodium sulfate and evaporated to dryness to give 24.9 g of an oil.

TLC: Rf=0.79, silica gel, ethyl acetate/pyridine/acetic acid/water 63/20/6/11 v/v/v/v.

(b) Teoc—Ppa(Boc)—N(Me)OMe

To a solution of 29.8 g of Teoc—Ppa(Boc)—OH and 7.54 g of N,O-dimethyl-hydroxylamine hydrochloride in 370 ml of dichloromethane was added 23 g of O-(benzotriazol-1-yl)-N,N,N',N'-tetramethyluronium tetrafluoroborate and 20.2 ml of tfiethylamine and the mixture was stirred for 2 hours. The reaction mixture was extracted with water and aqueous 0.9 M sodium hydrogencarbonate, dried with magnesium sulphate and concentrated. The residue was chromatographed on silica gel with 0→5% methanol in dichloromethane to give 32.2 g of the title compound.

TLC: Rf=0.42,silica gel, toluene/acetone 3/1 v/v.

(c) Teoc—Ppa(Boc)-(2-thiazolyl)

70 ml of n-Butyllithium (0.72 M in diethyl ether) was added dropwise to a cooled (−78° C.) solution of 4.55 ml of freshly distilled 2-bromothiazole in 40 ml of diethyl ether. The reaction mbiture was stirred for an additional 15 minutes whereupon 7.2 g of Teoc—Ppa(Boc)—N(Me)OMe dissolved in 40 ml tetrahydrofran was added slowly. After stirring for 30 min the reaction mbiture was poored into aqueous sodium hydrogencarbonate solution (200 ml). The ether layer was separated and the aqueous layer was extracted with ether. The combined ether extracts were washed with water, dried on magnesium sulphate and concentrated. The residue was pufified by silica gel chromatography to give 6.43 g of the title compound.

TLC: Rf=0.61, silica gel, in toluene/acetone 3/1 v/v.

(d) Teco—Ppa—(2-thiazolyl).TsOH 3.16 g p-Toluenesulphonic acid (1 H$_2$O) was added to a solution of 8 g of Teoc—Ppa(Boc)-(2-thiazolyl) in 116 ml diethyl ether. The mixture was slowly concentrated on a rotavapor at 30° C. The oily residue was stirred for an additional 2 hours on the rotavapor in vacuo to give 9.2 g of the p-toluenesulphonate salt.

TLC: Rf=0.6, silica gel, ethyl acetate/pyridine/acetic acid/water 63/20/6/11 v/v/v/v.

(e) Immobilisation of Teoc—Ppa—(2-thiazolyl).TsOH on hydroxymethyl polystyrene (Teoc—Ppa(C(O)OCH$_2$Pol)-(2-thiazolyl))

To a suspension of 10.0 g of hydroxymethyl polystyrene (HOCH$_2$Pol) (0.97 mM/g) and 12.9 g of di(N-succinimidyl) carbonate in acetonitrile (50 ml) and dichloromethane (50 ml) was added 7 ml triethylamine. The resulting mixture was shaken for 2 hours at room temperature. The resin was filtered, washed successively with dichloromethane, 1-methyl-2-pyrrolidinone and dichloromethane. The resin was resuspended in acetonittile (50 ml) and dichloromethane (50 ml). Then, 8.3 g Teoc—Ppa—(2-thiazolyl).TsOH and 3.7 ml of triethyl amine were added and the mixture was shaken for 17 hours. The resin was collected by filtration, washed successively with dichloromethane, 1-methyl-2-pyrrolidinone, dichloromethane and diethyl ether, and dried in vacuo tot give 13.3 g of resin.

(f) H—Ppa(C(O)OCCH$_2$Pol)-(2-thiazolyl).HCl 1.5 ml of a mixture of trifluoroacetic acid and dichloromethane (1:1 v/v) was added to 50 mg of Teoc—Ppa(C(O)OCH$_2$Pol)-(2-thiazolyl) and the reaction mixture was shaken for 30 min. The resin was filtered, washed with dichioromethane, 0.5 M HCl in dioxane-dichloromethane (1/7 v/v) and dichioromethane.

(g) Boc—Phe—Ppa(C(O)OCH$_2$Pol)-(2-thiazolyl)

To a solution of 40 mg of Boc—Phe—OH and 20 mg of 1-hydroxybenzotriazole in 1-methyl-2-pyrrolidinone (1 ml) was added 23 µl of N,N-diisopropylcarbodiimide. After stirring for 5 min the mixture was added to the resin. Then, 5 µl of 4-methyl morpholine was added and the resulting suspension was shaken for 2 hours, filtered, washed with 1-methyl-2-pyrrolidinone, dichloromethane and diethyl ether. Other N—t-butyloxycarbonyl arniocarboxylic acids were attached in the same fashion.

(h) H—Phe—Ppa(C(O)OCH$_2$Pol)-(2-thiazolyl).HCl

Removal of the N—t-butyloxycarbonyl groups from Boc—Phe—Ppa(C(O)OCH$_2$Pol)-(2-thiazolyl) performed in a similar fashion as described above for the removal of the Teoc group of Teoc—Ppa(C(O)OCH$_2$Pol)-(2-thiazolyl).

(i) N—(t-butloxycarbonylnmethyl)—N—Boc—D—Cha—Phe—Ppa(C(O)OCH$_2$Pol)-(2-thiazolyl)

N—(t-Butoxycarboxymethyl)—N—Boc—D—Cha—OH was attached to H—Phe—Ppa(C(O)OCH$_2$Pol)-(2-thiazolyl).HCl in a similar fashion as described above for the attachment of Boc—Phe—OH with H—Ppa(C(O)OCH$_2$Pol)-(2-thiazolyl).

(j) HOOC—CH$_2$—D—Cha—Phe—Ppa—(2-thiazolyl)

The resin was treated with 1 ml trifluoroacetic acid/thioanisole 10/1 v/v and shaken for 4 hours The reaction mixture was filtered, washed with trifluoroacetic acid and toluene. The combined filtrate and washings were concentrated. Heptane was added to the residue and the mixture was vortexed vigorously. The heptane layer was removed and the insoluble oily residue was washed with heptane. After drying in vacuo the residue was redissolved in water, filtered through a 0.45µ filter and lyophilized. The crude peptide was purified by preparative size exclusion chromatography (column; Superdex Peptide HR10/30; flow: 0.75 ml/min; eluent: water/acetonitrile 4/1 v/v). Lyophilisation of the appropriate fractions gave 6.4 mg of HOOC—CH$_2$—D—Cha—Phe—Ppa—(2-thiazolyl).

(k) HOOC—CH$_2$—D—Cha—X—Ppa—(2-thiazolyl) (table 62)

Compounds of formula HOOC—CH$_2$—D—Cha—X—Ppa—(2-thiazolyl) were prepared as described for HOOC—

CH₂—D—Cha—Phe—Ppa—(2-thiazolyl). All compounds were characterised by reversed-phase liquid chromatography on a Supelcosil LC-18-DB column using the following conditions: flow: 1.0 ml/min; buffer A: 0.5 M potassium phosphate buffer (pH 2.1); buffer B: water, buffer D: acetonitrile-water (9:1). Gradient: 0→30 min: 20% A/65% B/15% D to 20% A/25% B/55% D. UV-detection at 210 nm. Retention times in Table 62 are recorded in minutes.

TABLE 62

[Structural formula of compound with cyclohexyl group, thiazolyl group, and X—NH linker]

| X | Retention time | X | Retention time |
|---|---|---|---|
| (a) Phe | 27.5 | (h) Thr | 15.8 |
| (b) Pro | 21.7/23.8 | (i) Gly | 18.5/19.9 |
| (c) Ini | 20.7/21.1 | (j) Gln | 15.8/16.6 |
| (d) Sar | 20.3 | (k) Orn | 12.0/12.8 |
| (e) Ile | 15.7 | (l) Glu | 17.8/19.3 |
| (f) D-Phe | 21.8 | (m) Cha | 20.8 |
| (g) β-Ala | 19.0/19.5 | | |

Ini = isonipecotic acid (4-piperidinecarboxylic acid)
Sar = sarcosine (N-methylglycine)
Orn = ornithine (S-(+)-2,5-diaminopentanoic acid)

EXAMPLE 63

The following compounds can be prepared by using the methods of the present invention:

N—Me—D—Phe—Pro—Ppa—(2-thiazolyl)
HOOC—CH₂—D—Phe—Pro—PpaΨ[COCO]—OH
HOOC—CH₂—D—Phe—Pro—Ppa—(2-thiazolyl)
HOOC—CH₂—D—Cha—(N-cyclopentyl)—Gly—Ppa—(2-thiazolyl)
HOOC—CH₂—D—Cha—Pec—PpaΨ[COCO]—OH
HOOC—CH₂—D—Cha—Pec—Ppa—(2-thiazolyl)
HOOC—CH₂—D—Cha—(N-cyclohexyl)—Gly—PpaΨ[COCO]—OH
HOOC—CH₂—D—Cha—(N-cyclohexyl)—Gly—Ppa—(2-thiazolyl)
HOOC—CH₂—D—Cha—(N-cyclpropyl)—Gly—PpaΨ[COCO]—OH
HOOC—CH₂—D—Cha—(N-cyclopropyl)—Gly—Ppa—(2-thiazolyl)
N—Me—D—Phe—(N-cyclopentyl)—Gly—PpaΨ[COCO]—OH
N—Me—D—Phe—(N-cyclopentyl)—Gly—Ppa—(2-thiazolyl)
2-propyl-pentanoyl-Asp(OMe)—Pro—PpaΨ[COCO]—OH
2-propyl-pentanoyl-Asp(OMe)—Pro—Ppa—(2-thiazolyl)
2-propyl-pentanoyl-Asp—Pro—PpaΨ[COCO]—OH
2-propyl-pentanoyl-Asp—Pro—Ppa—(2-thiazolyl)
1-Piq—(N-cyclopentyl)—Gly—PpaΨ[COCO]—OH
1-Piq—(N-cyclopentyl)—Gly—Ppa—(2-thiazolyl)
Diphenylpropionyl—Pro—Ppa—(2-thiazolyl)
N—Me—D—Nle—Pro—PpaΨ[COCO]—OH
N—Me—D—Nle—Pro—Ppa—(2-thiazolyl)
EtSO₂—D—Phe—Pro—PpaΨ[COCO]—OH
EtSO₂—N(Me)—D—Cha—Pro—PpaΨ[COCO]—OH
EtSO₂—N(Me)—D—Cha—Pro—Ppa—(2-thiazolyl)
EtSO₂—N(Me)—D—Cha—Pro—Ppa—(2-oxazolyl)
HOOC—CH₂—N(Me)—D—Cha—Pro—PpaΨ[COCO]—OH
HOOC—CH₂N(Me)—D—Cha—Pro—Ppa—(2-thiazolyl)
HOOC—CH₂—N(Me)D—Cha—Pro—Ppa—(2-oxazolyl)

EXAMPLE 64
Anti-thrombin assay

Thrombin (Factor IIa) is a factor in the coagulation cascade. The anti-thrombin activity of compounds of the present invention was assessed by measring spectrophotometrically the rate of hydrolysis of the chromogenic substrate s-2238 exterted by thrombin. Ths assay for anti-thrombin activity in a buffer system was used to assess the $IC_{50}$-value of a test compound.

Test medium: Trometbine-NaCl-polyethylene glycol 6000 (TNP) buffer. Reference compomd: 12581 (Kabi) Vehicle: TNP buffer. Solubilisation can be assisted with dimethylsulphoxide, methanol, ethanol, acetonitrile or tert.-butyl alcohol which are without adverse effects in concentrations up to 2.5% in the final reaction mixture.

Technique

Reagents*: 1. Tromethamine-NaCl (TN) buffer. Composition of the buffer: Tromethaine (Tris) 6.057 g (50 mmol), NaCl 5.844 g (100 mmol), water to 1 l. The pH of the solution is adjusted to 7.4 at 37° C. with HCl (10 mmol·l⁻¹). 2. TNP buffer: Polyethylene glycol 6000 is dissolved in TN buffer to give a concentration of 3 g·l⁻¹ 3. S-2238 solution: One vial S-2238 (25 mg; Kabi Diagnostica, Sweden) is dissolved in 20 ml TN buffer to give a concentration of 1.25 mg·ml⁻¹ (2 mmol l⁻¹). 4. Thrombin solution: Human thrombin (16 000 nKat·vial⁻¹; Centraal Laboratorium voor Bloedtransfusie, Amsterdam, The Netherlands) is dissolved in TNP buffer to give a stock solution of 835 nKat·ml⁻¹. Immediately before use this solution is diluted with TNP buffer to give a concentration of 3.34 nKat·ml⁻¹.

*All ingredients used are of analytical grade

For aqueous solutions ultrapure water (Milli-Q quality) is used.

Preparation of test and reference compound solutions

The test and reference compounds are dissolved in Milli-Q water to give stock concentrations of $10^{-2}$ mol·l⁻¹. Each concentration is stepwise diluted with the vehicle to give concentrations of $10^{-3}$, $10^{-4}$ and $10^{-5}$ mol·l⁻¹. The dilutions, including the stock solution, are used in the assay (fina concentrations in the reaction mixture: $3·10^{-3}$; $10^{-3}$; $3·10^{-4}$; $3·10^{-5}$; $10^{-5}$; $3·10^{-6}$ and $10^{-6}$ mol·l⁻¹, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is preheated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories).

All data are collected in an IBM personal computer using LOTUS-MEASURE. For each compound concentration (expressed in mol·l$^{-1}$ reaction mixture) and for the blank the absorbance is plotted versus the reaction time in min.

Evaluation of responses: For each final concentration the maximum absorbance was calculated from the assay plot. The IC$_{50}$-value (final concentration, expressed in μmol·l$^{-1}$, causing 50% inhibition of the maximum absorbance of the blank) was calculated using the logit transformation analysis according to Hafier et al. (Arzneim.-Forsch.ADrug Res. 1977; 27(II): 1871–3).

In the following table, IC$_{50}$-values of compounds of the invention are listed:

| Example | IC$_{50}$-value (μM) |
|---|---|
| 3 | 0.54 |
| 15 | 0.95 |
| 31 | 0.245 |
| 38 | 1.8 |
| 47 | 2.83 |
| 53 | 2.6 |

What is claimed is:

1. A compound having the formula I

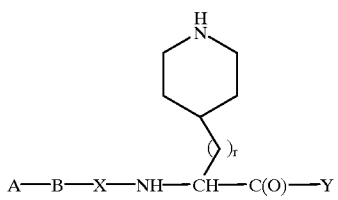

(I)

wherein

A is H, optionally substituted D,L α-hydroxyacetyl, R$^1$, R$^1$—O—C(O)—, R$^1$—C(O)—, R$^1$—SO$_2$—, R$^2$OOC—(CHR$^2$)$_m$—SO$_2$—, R$^2$OOC—(CHR$^2$)$_m$—, H$_2$NCO—(CHR$^2$)$_m$—, or an N-protecting group, wherein R$^1$ is selected from (1—12C)alkyl, (2–12C)alkenyl, (2–12C)alkynyl and (3–8C)cycloalkyl, which groups may optionally be substituted with (3–8C)cycloalkyl, (1–6C)alkoxy, oxo, OH, COOH, CF$_3$ or halogen, and from (6–14C)aryl, (7–15C)aralkyl and (8–16)aralkenyl, the aryl groups of which may optionally be substituted with (1–6C)alkyl, (3–8C)cycloalkyl, (1–6C)alkoxy, OH, COOH, CF$_3$ or halogen; each group R$^2$ is independently H or has the same meaning as R$^1$; m is 1, 2 or 3;

B is a bond, an amino acid of the formula —NH—CH [(CH$_2$)$_p$C(O)OH]—C(O)— or an ester derivative thereof with p being 0, 1, 2 or 3, —N((1–12C)alkyl)—CH$_2$—CO—, —N((2–12C)alkenyl)—CH$_2$—CO—, —N((2–12C)alkynyl)—CH$_2$—CO—, —N(benzyl)—CH$_2$—CO—, D-1-Tiq, D-3-Tiq, D—Atc, Aic, D-1-Piq, D-3-Piq or a L- or Damio acid having a hydrophobic, basic or neutral side chain, which amino acid may optionally be N-(1–6C)alkyl substituted; or A and B together are the residue R$^3$R$^4$N—CHR$^5$—C(O)—, wherein R$^3$ and R$^4$ independently are R$^1$, R$^1$—O—C(O)—, R$^1$—C(O)—, R$^1$—SO$_2$—, R$^2$OOC—(CHR$^2$)$_m$—SO$_2$—, R$^2$OOC—(CHR$^2$)$_m$—, H$_2$NCO—(CHR$^2$)$_m$—, or an N-protecting group, or one of R$^3$ and R$^4$ is connected with R$^5$ to form a 5- or 6-membered ring together with "N—C" to which they are bound, which ring may be fused with an aliphatic or aromatic 6membered ring; and R$^5$ is a hydrophobic, basic or neutral side chain;

X is an L-amino acid with a hydrophobic side chain, serine, threonine, a cyclic amino acid optionally containing an additional heteroatom selected from N, O or S, and optionally substituted with (1–6C)alkyl, (1–6C)alkoxy, benzyloxy or oxo, or X is —NR$^2$—CH$_2$—C(O)— or the fragment

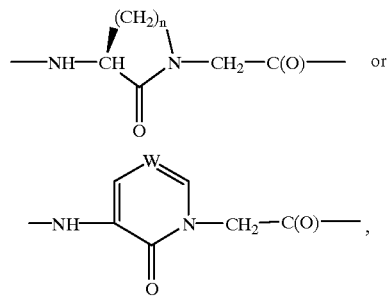

wherein n is 2, 3, or 4, and W is CH or N;

Y is H, —CHF$_2$, —CF$_3$, —CO—NH—(1–6C)alkylene-C$_6$H$_5$, —COOR$^6$ and R$^6$ being H or (1–6C)alkyl, —CONR$^7$R$^8$ and R$^7$ and R$^8$ being independently H or (1–6C)alyl or R$^7$ and R$^8$ together being (3–6C)alkylene, or Y is a heterocycle selected from 2-thiazole, 2-thiazoline, 2-benzothiazole, 2-oxazole, 2-oxazoline and 2-benzoxazole, which heterocycles may optionally be substituted with (1–6C)alkyl, phenyl, (1–6C)alkoxy, bennyloxy or oxo;

and r is 0, 1, 2 or 3;

or a prodrug thereof or a pharmaceutically acceptable salt thereof.

2. The compound of claim 1, wherein X is an L-amino acid with a hydrophobic side chain, serine, threonine or —NR$^2$—CH$_2$—C(O)—.

3. The compound of claim 1, wherein A is as previously defined;

B is a bond, an amino acid of the formula —NH—CH [(CH$_2$)$_p$C(O)OH]—C(O)— or an ester derivative thereof with p being 0, 1, 2 or 3, —N((1–6C)alkyl)—CH$_2$—CO—, —N((2–6C)alkenyl)—CH$_2$—CO—, —N(benzyl)—CH$_2$—CO—, D-1-Tiq, D-3-Tiq, D—Atc, Aic, D1Piq, D-3-Piq or a D-amino acid having a hydrophobic side chain, which amino acid may optionally be N-(1–6C)alkyl substituted;

or A and B together are the residue R$^3$R$^4$N—CHR$^5$—C(O)—;

and X is a cyclic amino acid optionally containing an additional heteroatom selected from N, O or S, and optionally substituted with (1–6C)alkyl, (1–6C)alkoxy, benzyloxy or oxo, or X is —NR$^2$—CH$_2$—C(O)— or the fragment

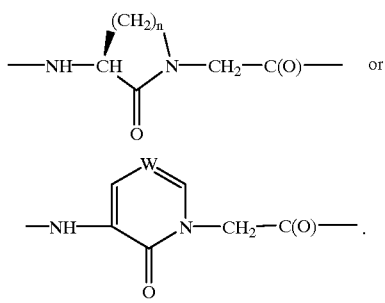

4. The compound of claim 3, wherein A is H, 2-hydroxy-3-cyclohexyl-propionyl-, 9-hydroxy-fluorene-9-carboxyl, $R^1$, $R^1$—$SO_2$—, $R^2OOC$—$(CHR^2)_m$—$SO_2$—, $R^2OOC$—$(CH^2)_m$—, $H_2NCO$—$(CHR^2)_m$—, or an N-protecting group, wherein $R^1$ is selected from (1–12C)alkyl, (2–12C)alkenyl, (6–14C)aryl, (7–15C)aralkyl and (8–16)aralkenyl; each group $R^2$ is independently H or has the same meaning as $R^1$;

B is a bond, D-1-Tiq, D-3-Tiq, D—Atc, Aic, D-1-Piq, D-3-Piq or a D-amino acid having a hydrophobic side chain, which amino acid may optionally be N-(1–6C)alkyl substituted;

or A and B together are the residue $R^3R^4N$—$CHR^5$—C(O)—;

Y is —CO—NH(1–6C)alkylene-$C_6H_5$, —$COOR^6$, —$CONR^7R^8$, or Y is a heterocycle selected from 2-thiazole, 2-thiazoline, 2-benzothiazole, 2-oxazole, 2-oxazoline and 2-benzoxazole.

5. The compound of claim 4, wherein A is H, $R^1$—$SO_2$— or $R^2OOC$—$(CHR^2)_m$—;

B is a bond, D-1-Tiq, D-3-Tiq, D—Atc, Aic, D-1-Piq, D-3-Piq or a D-amino acid having a hydrophobic side chain;

or A and B together are the residue $R^3R^4N$—$CHR^5$—C(O)—, wherein at least one of $R^3$ and $R^4$ is $R^2OOC$—$(CHR^2)_m$— or $R^1$—$SO_2$— and the other independently is (1–12C)alkyl, (2–12C)alkenyl, (2–12C)alkynyl, (3–8C)cycloalkyl, (7–15C)aralkyl, $R^1$—$SO_2$— or $R^2OOC$—$(CHR^2)_m$—, and $R^5$ is a hydrophobic side chain; and Y is —CO—NH—(1–6C)alkylene-$C_6H_5$, —$COOR^6$ with $R^6$ being H or (1–3C)alkyl, —$CONR^7R^8$, with $R^7$ and $R^8$ being independently H or (1–3C)alkyl or $R^7$ and $R^8$ together being (3–5C)alkylene, or Y is a heterocycle selected from 2-thiazole, 2-benzothiazole, 2-oxazole or 2-benzoxazole.

6. The compound of claim 5, wherein A is $R^2OOC$—$(CHR^2)_m$—;

B is a D-amino acid having a hydrophobic side chain;

or A and B together are the residue $R^3R^4N$—$CHR^5$—C(O)—, wherein at least one of $R^3$ and $R^4$ is $R^2OOC$—$(CHR^2)_m$— and the other independently is (1–12C)alkyl, (2–6C)alkenyl, (3–8C)cycloalkyl, benzyl, $R^1$—$SO_2$— or $R^2OOC$—$(CHR^2)_m$—;

and X is 2-azetidine carboxyric acid, proline, pipecolic acid, 4-thiazolidine carboxylic acid, 3,4-dehydro-proline, 2-octahydroindole carboxylic acid or —[N(3–8C)cycloalkyl]—$CH_2$—C(O)—.

7. The compound of claim 6, wherein A is HOOC—$CH_2$;

B is D—Phe, D—Cha, D—Coa, D—Dpa, p—Cl—D—Phe, p—OMethyl—D—Phe, p—OEthyl—D—Phe, D—Nle, m—Cl—D—Phe, 3,4-di—OMe—D—Phe, or D—Chg;

or A and B together are the residue $R^3R^4N$—$CHR^5$—C(O)—, wherein at least one of $R^3$ and $R^4$ is HOOC—$CH_2$— and the other independently is (1–4C)alkyl, (1–4C)alkyl-$SO_2$— or HOOC—$CH_2$— and $R_5$ is (3–8C)cycloalkyl, (3–8C)cycloalkyl(1–4C)alkyl, phenyl, benzyl, optionally substituted with chlorine or (1–4C)alkoxy.

8. The compound of claim 7, wherein A is HOOC—$CH_2$; B is D—Cha; X is proline or —[N(cyclopentyl)]—$CH_2$—C(O)—.

9. The compound of claim 5, wherein A is $R^1$—$SO_2$—;

B is a bond, D-1-Tiq, D-3-Tiq, D—Atc, Aic, D-1-Piq, D-3-Piq or a D-amino acid having a hydrophobic side chain;

or A and B together are the residue $R^3R^4N$—$CHR^5$—C(O)—, wherein at least one of $R^3$ and $R^4$ is $R^1$—$SO_2$— and the other independently is (1–12C)alkyl or $R^1$—$SO_2$—; and X is 2-azetidine carboxylic acid, proline, pipecolic acid, 4-thiazolidine carboxylic acid, 3,4-dehydro-proline, 2-octahydroindole catboxylic acid, —[N(3–8C)cycloalkyl]—$CH_2C(O)$—, or the fragment

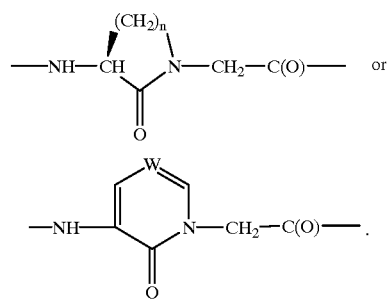

10. The compound of claim 9, wherein A is Ethyl-$SO_2$— or Benyl-$SO_2$—;

B is a bond, D—Phe, D—Cha, D—Coa, D—Dpa, p—Cl—D—Phe, p—OMethyl—D—Phe, p—OEthyl—D—Phe, D—Nle, m—Cl—D—Phe, 3,4-di—OMe—D—Phe, D—Chg; or or A and B together are the residue $R^3R^4N$—$CHR^5$—C(O)—, wherein at least one of $R^3$ and $R^4$ is Ethyl-$SO_2$— or Benzyl-$SO_2$— and the other independently is (1–12C)alcyl or $R^1$—$SO_2$— and $R^5$ is (3–8C)cycloalkyl, (3–8C)cycloalkyl(1–4C)akyl, phenyl, benzyl, diphenylmethinyl, which groups are optionally substituted with chlorine or (1–4C)alkoxy.

11. The compound of claim 10, wherein A is Ethyl-$SO_2$—, B is D—Cha, and X is proline or [N(cyclopentyl)]—$CH_2$—C(O)—.

12. The compound of claim 1, wherein r is 1.

13. A pharmaceutical composition comprising a compound of claim 1 and pharmaceutically suitable auxiliaries.

14. A method for treating or preventing a thrombin-related disease, comprising administering to a patient in need thereof an effective amount of a compound according to claim 1.

15. A method for producing a pharmaceutical composition, comprising admixing a compound according to claim 1 with pharmaceutically suitable auxiliaries.

* * * * *